(12) United States Patent
Badhwar et al.

(10) Patent No.: US 11,129,711 B2
(45) Date of Patent: Sep. 28, 2021

(54) DOUBLE COMPONENT MANDREL FOR ELECTROSPUN STENTLESS, MULTI-LEAFLET VALVE FABRICATION

(71) Applicant: University of Pittsburgh—Of the Commonwealth System of Higher Education, Pittsburgh, PA (US)

(72) Inventors: Vinay Badhwar, Sewickley, PA (US); Young Jae Chun, Pittsburgh, PA (US); Antonio D'Amore, Pittsburgh, PA (US); William R. Wagner, Gibsonia, PA (US)

(73) Assignees: University of Pittsburgh—Of the Commonwealth System of Higher Education; Ri.MED Foundation

( * ) Notice: Subject to any disclaimer, the term of this patent is extended or adjusted under 35 U.S.C. 154(b) by 0 days.

(21) Appl. No.: 15/553,799

(22) PCT Filed: Feb. 26, 2016

(86) PCT No.: PCT/US2016/019837
§ 371 (c)(1),
(2) Date: Aug. 25, 2017

(87) PCT Pub. No.: WO2016/138416
PCT Pub. Date: Sep. 1, 2016

(65) Prior Publication Data
US 2018/0071087 A1      Mar. 15, 2018

Related U.S. Application Data

(60) Provisional application No. 62/126,040, filed on Feb. 27, 2015.

(51) Int. Cl.
  *A61F 2/24* (2006.01)
  *D01D 5/00* (2006.01)
  (Continued)

(52) U.S. Cl.
  CPC .......... *A61F 2/2415* (2013.01); *A61F 2/2418* (2013.01); *A61L 27/18* (2013.01);
  (Continued)

(58) Field of Classification Search
  CPC .................................. A61F 2/24; A61L 27/18
  See application file for complete search history.

(56) References Cited

U.S. PATENT DOCUMENTS 3,320,972 A    5/1967   High et al.
4,902,508 A    2/1990   Badylak et al.
(Continued)

FOREIGN PATENT DOCUMENTS

EP    2599858 A2    6/2013
JP    2005507464 A  3/2005
(Continued)

OTHER PUBLICATIONS

Agarwal et al.; "Progress in the Field of Electrospinning for Tissue Engineering Applications"; Advanced Materials; 2009; pp. 3343-3351; vol. 21.
(Continued)

*Primary Examiner* — Matthew W Schall
(74) *Attorney, Agent, or Firm* — The Webb Law Firm

(57) ABSTRACT

Provided herein is a mandrel for use in electrospinning prosthetic valve devices. Also provided are prosthetic valve devices for implantation in an animal or a human. Methods of making and using the valve devices are also provided herein.

12 Claims, 21 Drawing Sheets

(51) Int. Cl.
  *A61L 27/18* (2006.01)
  *A61L 27/50* (2006.01)
  *A61L 27/58* (2006.01)
(52) U.S. Cl.
  CPC ............ *A61L 27/507* (2013.01); *A61L 27/58* (2013.01); *D01D 5/0076* (2013.01); *A61F 2/2409* (2013.01); *A61F 2210/0004* (2013.01); *A61F 2210/0014* (2013.01); *A61F 2230/0006* (2013.01); *A61F 2230/0008* (2013.01); *A61F 2250/0043* (2013.01); *A61F 2250/0067* (2013.01); *A61L 2430/20* (2013.01)

(56) References Cited

U.S. PATENT DOCUMENTS

| | | |
|---|---|---|
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,245,105 B1 | 6/2001 | Nguyen et al. |
| 6,458,153 B1 | 10/2002 | Bailey et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 7,041,132 B2 | 5/2006 | Quijano et al. |
| 7,112,293 B2 | 9/2006 | Dubson et al. |
| 7,175,656 B2 | 2/2007 | Khairkhahan |
| 7,276,271 B2 | 10/2007 | Dubson et al. |
| 7,455,689 B2 | 11/2008 | Johnson |
| 7,611,534 B2 | 11/2009 | Kapadia et al. |
| 7,803,184 B2 | 9/2010 | McGuckin, Jr. et al. |
| 7,914,569 B2 | 3/2011 | Nguyen et al. |
| 7,993,394 B2 | 8/2011 | Hariton et al. |
| 8,080,054 B2 | 12/2011 | Rowe |
| 8,470,023 B2 | 6/2013 | Eidenschink et al. |
| 8,475,525 B2 | 7/2013 | Maisano et al. |
| 8,623,079 B2 | 1/2014 | Savage et al. |
| 2005/0075725 A1 | 4/2005 | Rowe |
| 2006/0253192 A1 | 11/2006 | Atala et al. |
| 2007/0269481 A1 | 11/2007 | Li et al. |
| 2008/0109070 A1 | 5/2008 | Wagner et al. |
| 2008/0131965 A1 | 6/2008 | Baaijens |
| 2008/0243245 A1 | 10/2008 | Thambar et al. |
| 2008/0260831 A1 | 10/2008 | Badylak et al. |
| 2008/0268019 A1 | 10/2008 | Badylak et al. |
| 2009/0038761 A1 | 2/2009 | Seddon |
| 2010/0249922 A1 | 9/2010 | Li et al. |
| 2011/0082545 A1 | 4/2011 | Freund |
| 2012/0059454 A1 | 3/2012 | Millwee et al. |
| 2012/0101572 A1 | 4/2012 | Kovalsky et al. |
| 2012/0136430 A1 | 5/2012 | Sochman et al. |
| 2013/0035759 A1 | 2/2013 | Gross et al. |
| 2014/0100653 A1 | 4/2014 | Savage et al. |
| 2014/0128969 A1 | 5/2014 | Hill et al. |
| 2014/0207250 A1 | 7/2014 | O'Hare et al. |
| 2014/0243894 A1 | 8/2014 | Groothuis et al. |

FOREIGN PATENT DOCUMENTS

| | | |
|---|---|---|
| JP | 2006158494 A | 6/2006 |
| JP | 2007522829 A | 8/2007 |
| JP | 2009524507 A | 7/2009 |
| WO | 2010041944 A1 | 4/2010 |
| WO | 2011106137 A1 | 9/2011 |
| WO | 2011150328 A1 | 12/2011 |
| WO | 2012024390 A2 | 2/2012 |
| WO | 2014066365 A1 | 5/2014 |
| WO | 2014138194 A1 | 9/2014 |

OTHER PUBLICATIONS

Agarwal et al.; "Interventional Cardiology Perspective of Functional Tricuspid Regurgitation"; Circ Cardiovasc Interv; Dec. 2009; pp. 565-573; vol. 2.

Bloomfield et al.; "Twelve-Year Comparison of a Bjork-Shiley Mechanical Heart Valve With Porcine Bioprostheses"; The New England Journal of Medicine; Feb. 28, 1991; pp. 573-579; vol. 324, No. 9.

Bourke et al.; "Polymers derived from the amino acid L-tyrosine: polycarbonates, polyarylates and copolymers with poly(ethylene glycol)"; Advanced Drug Delivery Reviews; 2003; pp. 447-466; vol. 55.

Bryan et al.; "Prospective randomized comparison of CarboMedics and St. Jude Medical bileaflet mechanical heart valve prostheses: Ten-year follow-up"; The Journal of Thoracic and Cardiovascular Surgery; Mar. 2007; pp. 614-622; vol. 133.

Cobanoglu et al.; "Aortic Valve Replacement with the Starr-Edwards Prosthesis: A Comparison of the First and Second Decades of Follow-up"; Ann Thorac Surg; Mar. 1988; pp. 248-252; vol. 45.

Del Guadio et al.; "Electrospun bioresorbable heart valve scaffold for tissue engineering"; The International Journal of Artificial Organs; 2008; pp. 68-75; vol. 31, No. 1.

Fiordeliso et al.; "Design, synthesis, and preliminary characterization of tyros"; Journal of biomaterials science. Polymer edition; 1994; pp. 497-510; vol. 5, Issue 6.

Fujimoto et al.; "An Elastic, Biodegradable Cardiac Patch Induces Contractile Smooth Muscle and Improves Cardiac Remodeling and Function in Subacute Myocardial Infarction"; Journal of the American College of Cardiology; 2007; pp. 2292-2300; vol. 49, No. 23.

Gallegos et al.; "In-Vivo Experience with the Triflo Trileaflet Mechanical Heart Valve"; The Journal of Heart Valve Disease; Nov. 2006; pp. 791-799; vol. 15, Issue 6.

Gregoric et al.; "Preclinical Hemodynamic Assessment of a New Trileaflet Mechanical Valve in the Aortic Position in a Bovine Model"; The Journal of Heart Valve Disease; Mar. 2004; pp. 254-259; vol. 13, Issue 2.

Guan et al.; "Synthesis, characterization, and cytocompatibility of elastomeric, biodegradable poly(ester-urethane) ureas based on poly(caprolactone) and putrescine"; J Biomed Mater Res; 2002; pp. 493-503; vol. 61.

Hashizume et al.; "Morphological and mechanical characteristics of the reconstructed rat abdominal wall following use of a wet electrospun biodegradable polyurethane elastomer scaffold"; Biomaterials; 2010; pp. 3253-3265; vol. 31.

Hong et al.; "Tailoring the degradation kinetics of poly(ester carbonate urethane)urea thermoplastic elastomers for tissue engineering scaffolds"; Biomaterials; 2010; pp. 4249-4258; vol. 31.

Huang et al.; "A Library of L-Tyrosine-Derived Biodegradable Polyarylates for Potential Biomaterial Applications, Part I: Synthesis, Characterization and Accelerated Hydrolytic Degradation"; Journal of Biomaterials Science; 2009; pp. 935-955; vol. 20.

Kidane et al.; "Current Developments and Future Prospects for Heart Valve Replacement Therapy"; Journal of Biomedical Materials Research Part B: Applied Biomaterials; 2009; pp. 290-303; vol. 88B.

Kishimoto et al.; "Sutureless aortic valve replacement using a novel autologous tissue heart valve with stent (stent biovalve): proof of concept"; J Artif Organs; 6 Pages.

(56) References Cited

OTHER PUBLICATIONS

Koens et al.; "Part I: From a parameterized computer model of the aortic valve to a stentless 3D scaffold and functional evaluation."; Nov. 19, 2004; 14 Pages.

Lee et al.; "Nanofiber alignment and direction of mechanical strain affect the ECM production of human ACL fibroblast"; Biomaterials; 2005; pp. 1261-1270; vol. 26.

Mirnajafi et al.; "The flexural rigidity of the aortic valve leaflet in the commissural region"; Journal of Biomechanics; 2006; pp. 2966-2973; vol. 39.

Morsi et al.; "Current Developments and Future Challenges for the Creation of Aortic Heart Valve"; Journal of Mechanics in Medicine and Biology; 2008; pp. 1-15; vol. 8, No. 1.

O'Brien et al.; "Allograft Aortic Valve Replacement: Long-Term Follow-Up"; Ann Thorac Surg; 1995; pp. S65-S70; vol. 60.

Rogers; "Functional Tricuspid Regurgitation"; JACC: Cardiovascular Interventions; 2015; 3 Pages.

Rogers et al.; "Transatrial Intrapericardial Tricuspid Annuloplasty"; JACC: Cardiovascular Interventions; 2015; 9 Pages.

Sacks; "Biaxial Mechanical Evaluation of Planar Biological Materials"; Journal of Elasticity; 2000; pp. 199-246; vol. 61.

Sacks et al.; "Collagen fiber disruption occurs independent of calcification in clinically explanted bioprosthetic heart valves"; J Biomed Mater Res; 2002; pp. 359-371; vol. 62.

Schoen et al.; "Tissue Heart Valves: Current Challenges and Future Research Perspectives"; J Biomed Mater Res; 1999; pp. 439-465; vol. 47.

Schoen et al.; "Calcification of Tissue Heart Valve Substitutes: Progress Toward Understanding and Prevention"; Ann Thorac Surg; 2005; pp. 1072-1080; vol. 79.

Schoevaerdts et al.; "Twenty years' experience with the Model 6120 Starr-Edwards valve in the mitral position"; The Journal of Thoracic and Cardiovascular Surgery; Sep. 1987; pp. 375-382; vol. 94, Issue 3.

Simonet et al.; "Heart valve tissue regeneration"; 2011; pp. 202-224.

Simonet et al.; "Hemodynamic testing of a 3D electrospun heart valve prosthesis"; 2011; 2 Pages.

Soletti et al.; "A bilayered elastomeric scaffold for tissue engineering of small diameter vascular grafts"; Acta Biomaterialia; 2010; pp. 110-122; vol. 6.

Stankus et al.; "Hybrid nanofibrous scaffolds from electrospinning of a synthetic biodegradable elastomer and urinary bladder matrix"; J Biomater Sci Polym Ed.; 2008; pp. 635-652; vol. 19, No. 5.

Van Lieshout et al.; "Electrospinning versus knitting: two scaffolds for tissue engineering of the aortic valve"; J Biomater Sci Polymer Edn; 2006; pp. 77-89; vol. 17, No. 1-2.

Vongpatanasin et al.; "Prosthetic Heart Valves"; The New England Journal of Medicine; Aug. 8, 1996; pp. 407-416; vol. 335, No. 6.

Wells et al.; "Cyclic loading response of bioprosthetic heart valves: effects of fixation stress state on the collagen fiber architecture"; Biomaterials; 2005; pp. 2611-2619; vol. 26.

Wu et al.; "Mechanical heart valves: Are two leaflets better than one?"; The Journal of Thoracic and Cardiovascular Surgery; 2004; pp. 1171-1179; vol. 127, No. 4.

Xu et al.; "Aligned biodegradable nanofibrous structure: a potential scaffold for blood vessel engineering"; Biomaterials; 2004; pp. 877-886; vol. 25.

Yacoub et al.; "Fourteen-Year Experience With Homovital Homografts for Aortic Valve Replacement"; Journal of Thoracic and Cardiovascular Surgery; 1995; pp. 186-194; vol. 110.

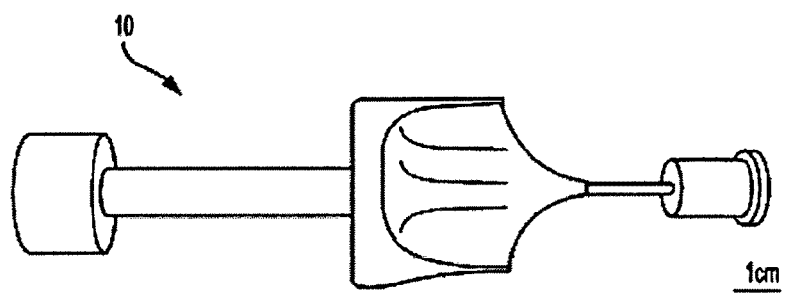
FIG. 1A
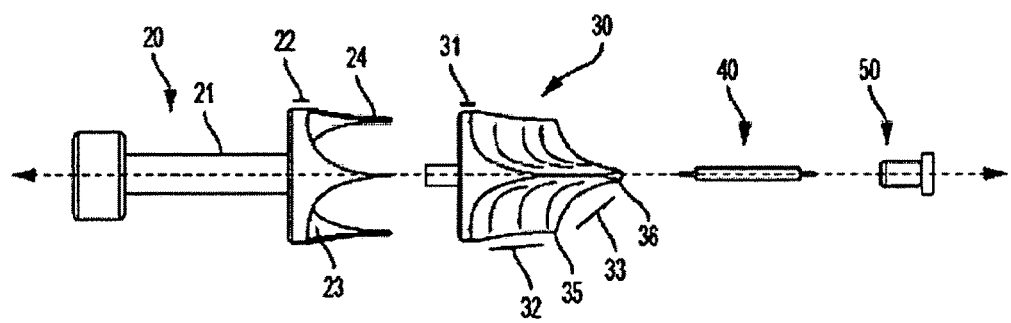
FIG. 1B
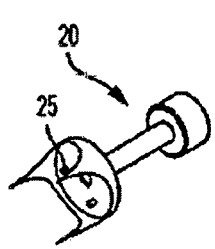 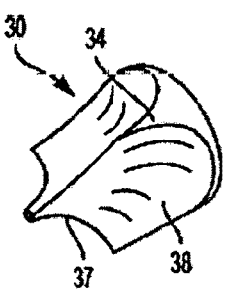 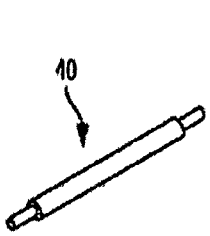 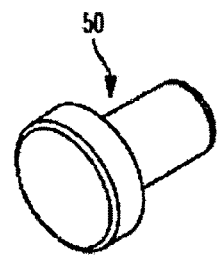
FIG. 1C　　FIG. 1D　　FIG. 1E　　FIG. 1F

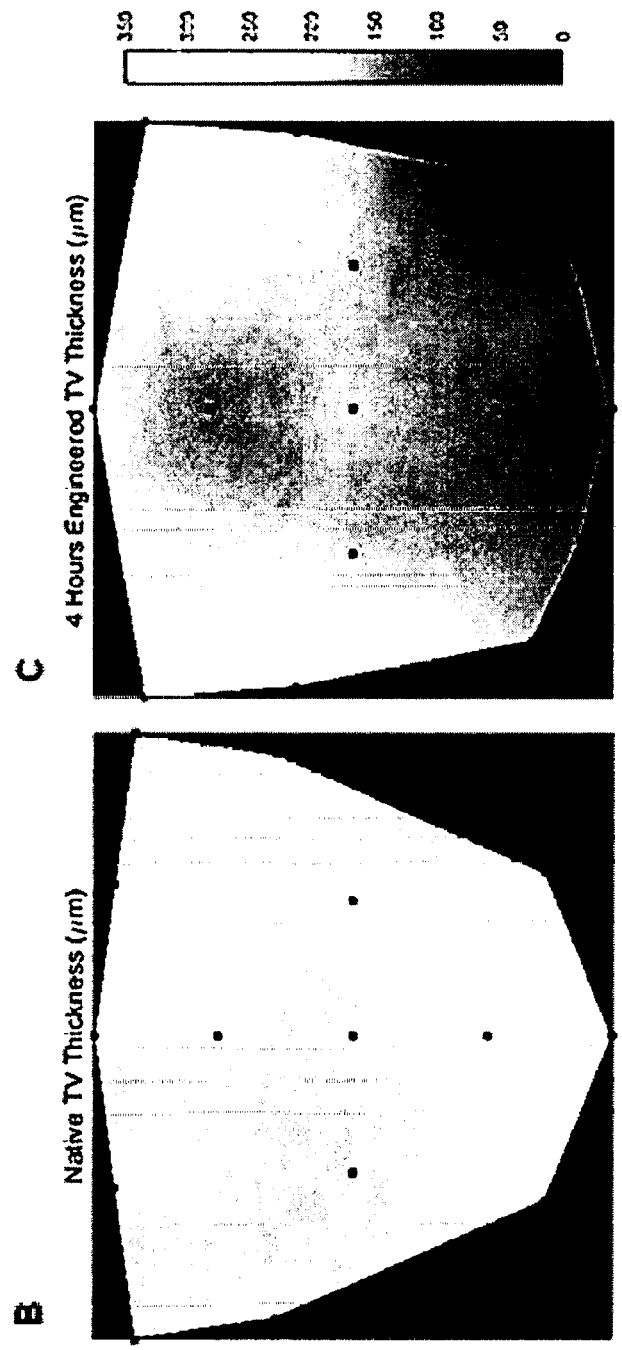

V1=0.3 m/s  V2=1.5 m/s  V3=3 m/s

DOUBLE COMPONENT MANDREL FOR ELECTROSPUN STENTLESS, MULTI-LEAFLET VALVE FABRICATION

CROSS REFERENCE TO RELATED APPLICATIONS

This application is a national stage of International Patent Application No. PCT/US2016/019837, file Feb. 26, 2016, which claims the benefit of U.S. Patent Provisional Application Ser. No. 62/126,040 filed Feb. 27, 2015, each of which is hereby incorporated by reference in its entirety.

The present disclosure is generally directed to a mandrel structure and a polymer electrodeposition method that is useful, for example, for preparation of prosthetic heart valves and other anatomical structures.

Congenital valve defects remain a burden for pediatric cardiac patients. Each year, 8/1000 infants are born with a congenital heart defect, affecting a total of approximately 1,000,000 Americans. Valve repair/replacement procedures may have limited durability, and require permanent anti-thrombogenic therapies (e.g. Coumadin, Pradaxa, Xarelto etc.). Most importantly, current materials (bovine pericardium, pyrolytic titanium, etc.) for heart valve repair or replacement are limited by the inability to grow or remodel.

Tissue engineered valves offer the potential to overcome these disadvantages by creating living structures that can undergo somatic growth, have reduced thrombogenicity, and proper coaptation levels under physiological conditions. However, tissue engineered valves are still limited by the availability of biocompatible scaffold materials with desirable degradation properties and biomechanical properties. The vast majority of the previous in vivo studies available in the tissue engineered literature involved seeded/non-seeded non-woven (e.g. polyglycolic acid (PGA): poly-L-lactic acid (PLLA) blends) scaffold. These prostheses were affected by several limitations including tissue shrinkage over time in vivo, progressive calcification, and valve regurgitation. Amorphous structure, absent or limited control over the material fibers structure are among the most critical causes for these limitations.

Electrospun leaflet fabrication such as the one presented in PCT Publication No. WO 2011/150328 A1 offers the opportunity to produce valve leaflets with controlled anisotropy. However, conventional fiber deposition on flat or cylindrical targets does not allow for: obtaining curvilinear fibers distribution mimicking the native valves' collagen micro-structure; fabricating leaflets with concave shape at rest, mimicking native anatomy; and fabricating a fully assembled multi-leaflet, stentless valve. Similarly, fiber deposition on complex geometries does not allow for control of the bending rigidity (out of plane mechanics) of the leaflets or full control over leaflets mechanical anisotropy (planar mechanics).

PCT Publication No. WO 2010/041944 A1, describes a method of preparing an electrospun valve. However, the described method and device do not allow for production of a unified valve-plus-conduit structure with superior control over leaflet physical parameters, such as anisotropy, fiber direction, rigidity, and thickness, which are parameters that are needed for formation of useful prosthetic valves.

Electrospinning of various materials is described, for example, in PCT Publication Nos. WO 2010/041944 and WO 2011/150328, and US Patent Application Publication Nos. 2008/0268019 and 2008/0109070). In a most general sense, electrodeposition, such as electrospinning, is the deposition of polymer fibers from an electrically-charged nozzle onto a target that has an opposite electrical charge, the electrical field causing the formation of and streaming of the fibers onto the target. The target can be a rotating object, referred to as a mandrel, or a non-rotating surface. Motion of the nozzle and or target, using standard two- or three-dimensional stages, robotics, motors, etc., including rotational motion, produces relative motion of the nozzle and target. Controlled electrodeposition of a polymer composition onto a target, such as a rotating mandrel target, poses significant technical hurdles. When the target, e.g., a mandrel, comprises concave portions (indentations extending toward a rotational axis), the rotation and longitudinal motion of the mandrel in relation to the nozzle supplying the polymer, prevents adequate control over the thickness, density, anisotropy and fiber quality within concave surfaces.

SUMMARY

The device and method provided herein overcome these limitations by introducing an electrodeposition target, such as a collecting mandrel design, that allows for superior control of electrodeposition on indented portions of the target.

In some aspects, the device includes a mandrel comprising a cylindrical surface and concave surfaces. By patterning conductive and non-conductive or less-conductive electrical insulator material onto the target, deposition of the polymer can be likewise patterned. Therefore, provided herein is an electrodeposition target comprising insulating and non-insulating surfaces, along with a method of preparing an electrodeposited object using that target.

In the device described herein, the collecting mandrel is used to fabricate a complete multi-leaflet, stentless valve prosthetic with variable shape (mitral, aortic, pulmonary, tricuspid, or with pathological malformations) and variable size. In some aspects, the design described herein provides (a) control over leaflets mechanical anisotropy (planar mechanics) by changing the mandrel tangential velocity; (b) control over leaflets bending rigidity (out of plane mechanics) by changing the mandrel linear velocity; (c) control over leaflets micro-fibers direction. (e.g., curvilinear fibers, the main direction of alignment is circumferential within the belly region and changes to axial toward the commissure regions); (d) the possibility to construct leaflets of concave shape mimicking native anatomy, where shape, thickness and size can be varied to duplicate human or animals healthy or pathological valves anatomy; and (e) the possibility to construct fully assembled multi-leaflet, stentless valve without a valve conduit.

In the electrospinning mandrel described herein, material deposition is concentrated only on desired areas by utilizing a non-electrical conductive (e.g., insulating) material. In the examples below, the material that was utilized was acrylonitrile butadiene styrene (ABS) and a conductive deposition are made of aluminum (material utilized: Aluminum 6061-T651). Previous implementations, such as that of PCT Publication No. WO 2010/041944 A1, are affected by excessive accumulation of material radially in close proximity of the polymer injection. In contrast, the device and method provided herein allow for the fabrication of stent-less valve by concentrating the deposition on the belly region of the leaflet. Thickness values of the leaflets produced are in the range 40-300 microns.

In some aspects, the device and method described herein provide: (a) a double component design made of a non-metallic component (shield, or insulator) and a metallic target; (b) control over leaflets mechanical anisotropy (planar mechanics) by changing the mandrel tangential velocity; (c) control over leaflets bending rigidity (out of plane mechanics) by changing the mandrel linear velocity; (d) control over leaflets micro-fibers direction. (e.g. curvilinear fibers, main direction of fibers alignment is circumferential within the belly region and changes to axial toward the commissure regions); (e) the ability to construct leaflets of concave shape mimicking native anatomy, shape and size can be varied to duplicate human or animals healthy or pathological valves anatomy; and (f) the ability to construct fully assembled multi-leaflet, stentless valve without a valve conduit.

In some aspects, the device provided herein includes an electrodeposition target. The target comprises a surface, and the surface comprises a pattern of conductive and non-conductive portions, wherein the target is attached to a mandrel having a rotational axis, and a spindle electrically connected to a conductive portion of the target. The mandrel, which, when in use, is rotated. In another aspect, the target comprises a support portion disposed about the rotational axis of the mandrel; a conductive insert comprising a plurality ridges extending longitudinally from the support portion and a plurality of concave portions between the ridges; and a non-conductive layer over at least a portion of the support portion and at least a portion of the ridges In some aspects, the insert comprises two concave portions, wherein the two concave portions are symmetrical or asymmetrical about a rotation axis of the mandrel. In another aspect, the concave portions of the insert have the shape of a normal or pathological valve leaflet (cusp), such as a shape and size of a normal or pathological human or animal mitral, tricuspid, aortic, or pulmonary valve cusp (leaflet). In some aspects, a three-leaflet portion is used to prepare a tricuspid valve. In another aspect, a two-leaflet portion is used to prepare a bicuspid valve.

In some aspects, prosthetic valve formed from a matrix of polymeric fibers, comprising a tubular (does not imply cylindrical, but can have a circular, oval or any closed shape in cross-section perpendicular to the longitudinal axis) support portion defining an aperture and having a longitudinal axis; and at least two concave leaflets extending longitudinally from the support portion, wherein each leaflet comprises a concave central portion, a peripheral portion about the concave central portion, a proximal end longitudinally connected to the support portion, and a distal end that is longitudinally distal to the support portion, wherein peripheral portions of adjacent leaflets are partially joined at and adjacent to the support portion forming commissures between adjacent leaflets.

In some aspects, a method of making a valve structure comprises electrodepositing a matrix of a biodegradable, biocompatible polymer composition onto the electrodeposition target.

In the assembled mandrel structure, the mandrel, annular region, and ridges are covered by the insulator ABS. The mandrel comprises three parts, a shield, prepared from the insulator, a conductive target, and a removable axial piece. A polymer, such as poly(ester-urethane)urea (PEUU), is electrodeposited about the conductive portion of the target, with some overlap with the insulating cover of the annular portion. The mandrel is placed in a chuck and is rotated and moved in a longitudinal direction. While in some aspects, the mandrel is rotated, and the electrodeposition nozzles are not rotated about the mandrel, the spatial location and relative orientation of the polymer nozzles and the mandrel can be controlled either manually, or they can be controlled by a computer, using standard robotics and stages.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 1A is schematic diagram of a double component three-leaflet version of a mandrel fully assembled, according to one aspect of the invention.

FIG. 1B is an exploded view of the double component mandrel of FIG. 1A, with, from left to right, a non-conductive plastic shield, a main collecting target, conducting shaft and axial support.

FIG. 1C is a perspective view of a non-conductive plastic shield of the mandrel of FIG. 1A.

FIG. 1D is a perspective view of a conductive insert with three-leaflet heart valve shape of the mandrel of FIG. 1A.

FIGS. 1E and 1F are perspective views of the conducting shaft and axial support of the mandrel of FIG. 1A.

FIG. 5(A) is a photographic image of a double component mandrel before the polymer fibers deposition. FIG. 5(B) is a photographic image of a double component mandrel after 3 hrs of polymer fibers deposition showing selective fibers deposition on main collecting target. FIG. 5(C) is a photographic image of the top view of a trileaflet valve removed from the mandrel showing the valve immersed in PBS with leaflets coaptation at rest. FIG. 5(D) is a schematic representation of an electrospinning fabrication configuration for tri-leaflets heart fabrication showing the position of the mandrel and its two motion modalities: ω mandrel rotational speed, ν mandrel linear velocity as well as the voltage generators and injectors/pump apparatus.

FIGS. 7B and 7C show thickness maps for (FIG. 7B) native porcine tricuspid valve thickness distribution over the leaflet area and for (FIG. 7C) an engineered tricuspid valve thickness distribution over the leaflet area after 3 hrs of fabrication. The thickness maps comparison (native vs. artificial) illustrates comparable leaflets thickness values over the entire surface.

FIGS. 13A and 13B show detected orifice areas (white) for the Carpentier-Edwards and Engineered Valve respectively during the systolic phase.

FIG. 13(C) is a bar graph representation of the bending deformation index (BDI) for the Carpentier-Edwards bioprosthethic valve and the engineered valve of FIGS. 15A and 15B, respectively. BDI, which is a widely adopted metric for bending rigidity (see "In vitro hydrodynamics, cusp-bending deformation, and root distensibility for different types of aortic valve-sparing operations: Remodeling, sinus prosthesis, and reimplantation" by A. Erasmi et al. in The Journal of Thoracic and Cardiovascular Surgery Volume 130, Issue 4, October 2005, pp. 1044-1049), was calculated at the mid-diastole point.

FIG. 13(D) is a bar graph representation of the geometric orifice area comparison (GEO) of the Carpentier-Edwards bioprosthethic valve and the engineered valve of FIGS. 15A and 15B, GEO were calculated from image processing illustrated in A-B at peak systole.

FIG. 13(E) is a bar graph representation of the max systolic pressure of the Carpentier-Edwards bioprosthethic valve and the engineered valve of FIGS. 15A and 15B.

FIG. 13(F) is a bar graph representation of the mean systolic pressure of the Carpentier-Edwards bioprosthethic valve and the engineered valve of FIGS. 15A and 15B.

FIG. 13(G) is a bar graph representation of the mean pressure drop across the Carpentier-Edwards bioprosthethic valve and the engineered valve of FIGS. 15A and 15B during a complete cycle including systole and diastole.

FIG. 13(H) is a bar graph representation of the mean flow across the Carpentier-Edwards bioprosthethic valve and the engineered valve of FIGS. 15A and 15B during a complete cycle including systole and diastole.

DETAILED DESCRIPTION

Figure 2A:
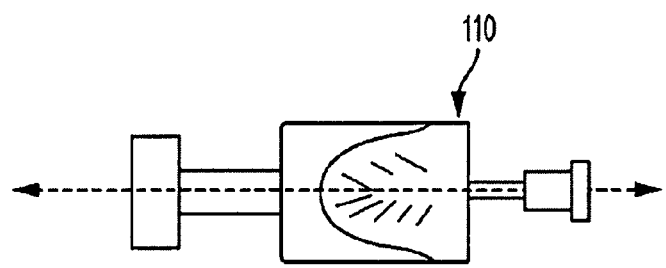
FIG. 2A is a schematic representation of a side view of a double component bileaflet version of a mandrel fully assembled, according to one aspect of the invention.

The use of numerical values in the various ranges specified in this application, unless expressly indicated otherwise, are stated as approximations as though the minimum and maximum values within the stated ranges are both preceded by the word "about." In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "comprising," "comprise" or "comprised," and variations thereof, are meant to be open ended. The terms "a" and "an" are intended to refer to one or more.

As used herein, the term "target" refers to points on the surface of an electrically charged object over which polymeric material is to be electrodeposited, or points on a surface adjacent thereto, such that in the absence of any insulator at any point on the target surface, or an adjacent point on the object, electrodeposition would be influenced by the presence of an electrical charge at that point during the course of electrodeposition. As such, the target does not include portions of the surface of the electrically charged object that, in the absence of an electrical insulator, an electrical charge at that portion of the surface of the electrically charged object would not influence the electrodeposition.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the term "patient" or "subject" refers to members of the animal kingdom including but not limited to human beings and "mammal" refers to all mammals, including, but not limited to human beings.

A biodegradable polymer composition is "biocompatible" in that the polymer and degradation products thereof are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain groups are missing and/or modified when incorporated into the polymer backbone. A polymer is said to comprise a specific type of linkage if that linkage is present in the polymer.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions, described herein. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of abdominal wall repair, it is desirable that the matrix dissolves over at least a week and preferably longer. More importantly, the matrix would have to retain its supportive capacity until tissue remodeling occurs, such as for at least 2-8 weeks, or longer.

The valve structures described herein are prepared from any biocompatible material. In certain examples below, the valve structures are prepared from a urethane, specifically a poly(ester-urethane)urea (PEUU), which was synthesized using putrescine as a chain extender and two-step solvent synthesis method described. Valve structures were fabricated with PEUU by electrospinning. PEUU features include high elasticity and mechanical strength coupled with controllable biodegradative and cell-adhesive properties. The polymer composition has found use in a number of in vivo scenarios including as a cardiac patch, in abdominal wall repair, and in vascular grafts. Alternative chemistries allow the polyurethanes to include added non-thrombogenic chemical moieties, and to use nondegradable polyurethanes as permanent structures not meant to be remodeled in situ. Additional biodegradable polymeric compositions are known in the art, and exhibit suitable strength and elasticity for use along with, or substituting for the described PEUU.

The valve structures optionally comprise a biodegradable, elastomeric polymer component and/or a biomacromolecular component, such as an extracellular matrix (ECM) gel.

In one aspect, the valve structures are prepared from a synthetic polymeric composition. In another, the polymeric composition combines a synthetic polymer with an ECM gel, such as described in PCT Publication No. WO 2012/024390. The ECM gel component, while useful in promoting cell growth (including, but not limited to one or more of colonization, propagation, infiltration, cell viability, differentiation, tissue repair), has insubstantial strength for use as a structural tissue repair scaffold in a patient. Where the synthetic polymer and ECM gel are mixed, any ratio of biodegradable, elastomeric polymer to ECM gel that shows excellent cellular infiltration, while displaying adequate tensile strength and elasticity may be used, for example a useful ratio of polymer to gel ranges from 70%-85%:15%-30%, including increments therebetween. This can be achieved by codepositing the biodegradable, elastomeric polymer and the ECM gel by electrospinning. For example, the synthetic biodegradable, elastomeric polymer is electrospun and the ECM gel is sprayed, e.g. electrosprayed.

In its broadest sense, to produce an ECM gel according to one non-limiting example, ECM-derived scaffold materials, e.g., decellularized or devitalized tissue, are communited and solubilized to form a hydrogel. In one example, the solubilized hydrogel is not dialyzed. Solubilization may be achieved by digestion with a suitable protease, such as the endoproteases trypsin, chymotrypsin, pepsin, papain and elastase. In certain non-limiting examples, the method for making such a gel comprises: (i) comminuting an extracellular matrix, (ii) solubilizing intact, non-dialyzed and/or non-cross-linked extracellular matrix by digestion with an acid protease in an acidic solution, e.g., at a pH of approximately 2.0 (e.g. 0.01N HCl), to produce a digest solution, (iii) raising the pH of the digest solution to a pH between 7.2 and 7.8 to produce a neutralized digest solution, and (iv) gelling the solution at a temperature greater than approximately 25° C.

"ECM material" is a material prepared from an extracellular matrix-containing tissue, and includes decellularized or devitalized tissue. ECM material can be used to produce gels according to the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666).

In certain examples, ECM material is decellularized tissue prepared from tissue of a vertebrate animal, for example and without limitation, from a mammal, including, but not limited to, human, monkey, pig, cow and sheep. The ECM material can be prepared from any organ or tissue, including without limitation, urinary bladder, intestine, liver, esophagus and dermis. In one example, the ECM material is decellularized tissue isolated from urinary bladder tissue. The ECM material may or may not include the basement membrane portion of the tissue. In certain examples, the ECM material includes at least a portion of the basement membrane. In certain examples, the ECM material is prepared from pericardium or valve leaflets obtained, fore example from a pig, cow, horse, monkey, or human, for example bovine pericardium or porcine valve leaflets.

As an example, decellularized tissue is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa can be removed by mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa can also be dissociated by soaking the tissue in a de-epithelializing solution, for example and without limitation, hypertonic saline. The resulting UBM comprises basement membrane of the tunica mucosa and the adjacent tunica propria.

In another example, the epithelial cells are delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one example, the decellularized tissue is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM material consists mainly of the tunica submucosa.

ECM material is decellularized, sterilized and/or dried by any useful method. The ECM material can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, ECM is disinfected by immersion in 0.1% (v/v) peracetic acid (a), 4% (v/v) ethanol, and 96% (v/v) sterile water for 2 h. The decellularized tissue is then washed twice for 15 min with PBS (pH=7.4) and twice for 15 min with deionized water.

Commercially available ECM materials derived from small intestinal submucosa or SIS include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another example, the ECM material is derived from dermis. Commercially available preparations include, but are not limited to Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another example, the ECM is derived from urinary bladder. Commercially available preparations include, but are not limited to UBM (Acell Corporation; Jessup, Md.).

In one non-limiting example, the decellularized tissue is lyophilized, comminuted, and is then solubilized with an acid protease. In certain aspects, the decellularized tissue is not dialyzed and/or is not crosslinked (subjected to a crosslinking method) prior to digestion with the acid protease. The acid protease may be, without limitation, pepsin or trypsin, and in one example is pepsin. The decellularized tissue typically is solubilized at an acid pH suitable or optimal for the protease, between pH 1.5 and 3, for example in a 0.01M HCl solution (pH ~2). The solution typically is solubilized for 12-48 hours, depending upon the tissue type, with mixing (stirring, agitation, admixing, blending, rotating, tilting, etc.). Once the decellularized tissue is solubilized the pH is raised to between 7.2 and 7.8, and according to one example, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution is gelled at temperatures approaching 37° C., typically at any temperature over 25° C., though gelation proceeds much more rapidly at temperatures over 30° C. and as the temperature approaches physiological temperature (37° C.). The method typically does not include a dialysis step prior to gelation, yielding a more-complete ECM-like matrix that typically gels at 37° C. more slowly than comparable collagen or dialyzed ECM preparations.

The ECM gel can be sprayed, for example, as a liquid or hydrogel and may be combined with other polymers, as described herein. An ECM gel is reverse-gelling, meaning it forms a hydrogel when its temperature is raised and may have an LCST (Lower Critical Solution Temperature) above or below the temperature at which the solution is sprayed, and as such will have a gel transition at a temperature higher, equal to or lower than the temperature at which the ECM gel is sprayed. For example, if the hydrogel is sprayed at room temperature (that is approximately 20-25° C.) or less and the LCST of the ECM material is greater than the spraying temperature, but, e.g., less than 37° C., the material can be sprayed and will later gel on warming. See, e.g. United States Patent Publication No. 20080260831, incorporated herein by reference for its technical disclosure. See also, Stankus et al., Hybrid nanofibrous scaffolds from electrospinning of a synthetic biodegradable elastomer and urinary bladder matrix, J Biomater. Sci. Polym. Ed. (2008) 19(5): 635-652. In the Stankus article, PEUU was mixed with solubilized UBM ECM and was electrospun.

Generally, polymeric components suitable for anatomical prosthetic structures described herein are any polymer that is biocompatible and can be biodegradable. In certain non-limiting examples, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold, where applicable. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting example, the polymer composition may comprise a biomacromolecular component derived from an ECM. For example, as described in further detail below, the polymer composition may comprise the biomacromolecule collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

A number of biocompatible, biodegradable elastomeric (co)polymers are known and have been established as useful in preparing cell growth matrices, including biodegradable poly(ester urethane) urea (PEUU), poly(ether ester urethane) urea (PEEUU), poly(ester carbonate)urethane urea (PECUU) and poly(carbonate)urethane urea (PCUU). In general, useful (co)polymers comprise monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

In certain aspects, the polymers used to make the structures described herein also release therapeutic agents when they degrade within the patient's body. For example, the individual building blocks of the polymers may be chosen such that the building blocks themselves provide a therapeutic benefit when released in situ through the degradation process. In one example, one of the polymer building blocks is putrescine, which has been implicated as a substance that causes cell growth and cell differentiation.

The biodegradable polymers may be, without limitation, homopolymers, copolymers, and/or polymeric blends. According to certain examples, the polymer(s) comprise, without limitation, one or more of the following monomers: glycolide, lactide, caprolactone, dioxanone, and trimethylene carbonate. According to certain examples, the polymer is chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polymer comprising urethane linkages, a polyurethane, a poly(ester urethane) urea, a poly(ether ester urethane) urea elastomer, a poly(ester carbonate urethane) urea, a poly(carbonate urethane) urea, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin. In one example, the polymer composition comprises a poly(ester urethane) urea with from about 25% wt. to about 75% wt. collagen. The polymer composition also may comprise elastin, collagen or a mixture thereof, for example and without limitation from about 25% wt. to about 75% wt. of a mixture of collagen and elastin, which are, according to one example, in approximately (about) equal amounts. In one non-limiting example, the polymer comprises a polycaprolactone. In another example, the polymer comprises a polycaprolactone diol. In yet another example, the polymer comprises a triblock copolymer comprising polycaprolactone, poly(ethylene glycol), and polycaprolactone blocks In another non-limiting example, the polymer composition comprises a biomacromolecular component derived from an ECM. For example, the polymer composition may comprise the biomacromolecule collagen so that collagenase, which is present in situ, can degrade the collagen. As an example, the polymer composition may comprise one or both of a collagen and an elastin. Collagen is a common ECM component and typically is degraded in vivo at a rate faster than many synthetic bioerodable polymers. Therefore, manipulation of collagen content in the polymer composition can be used as a method of modifying bioerosion rates in vivo. Collagen may be present in the polymer composition in any useful range, including, without limitation, from about 2% wt. to about 95% wt., for example in the range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition, In another example, the sum of the collagen and elastin content in the polymer composition is in any useful range, including, without limitation, from about 2% wt. to about 95% wt., for example in the range of from about 25% wt. to about 75% wt., inclusive of all ranges and points therebetween, including from about 40% wt. to about 75% wt., including about 75% wt. and about 42.3% wt.

In one non-limiting example, the polymer composition comprises a biodegradable poly(ester urethane) urea elastomer (PEUU). PEUU can be manufactured by reacting a diol with a diisocyanate to form a prepolymer and then reacting the prepolymer with a diamine. A non-limiting example of such a PEUU is an elastomeric polymer made from polycaprolactone diol ($M_W$ 2000) and 1,4-diisocyanatobutane, using a diamine chain extender such as putrescine. One non-limiting example or a method for preparing a PEUU polymer is a two-step polymerization process whereby polycaprolactone diol ($M_W$ 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one example, the diamine is putrescine, which is added drop-wise while stirring and allowed to react at room temperature for 18 hours. In one example, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting example, the polymer composition comprises poly(ether ester urethane) urea elastomer (PEEUU). For example and without limitation, the PEEUU may be made by reacting polycaprolactone-b-polyethylene glycol-b-polycaprolactone triblock copolymers with 1,4-diisocyanatobutane and putrescine. In one non-limiting example, PEEUU is obtained by a two-step reaction using a 2:1:1 reactant stoichiometry of 1,4-diisocyanatobutane:triblock copolymer:putrescine. According to one non-limiting example, the triblock polymer can be prepared by reacting poly(ethylene glycol) and ε-caprolactone with stannous octoate at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In another non-limiting example, the polymer composition comprises a poly(ester carbonate)urethane urea (PECUU) or a poly(carbonate)urethane urea (PCUU), which are described, for example, in Hong et al. (Tailoring the degradation kinetics of poly(ester carbonate urethane)urea thermoplastic elastomers for tissue engineering scaffolds Biomaterials, Biomaterials 31 (2010) 4249-4258). Poly(ester carbonate urethane)urea (PECUU) is synthesized, for example using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC): BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

Diamines and diols are useful building blocks for preparing the (co)polymer compositions described herein. Diamines as described above have the structure H2N—R—$NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as poly-caprolactone-PEG copolymers, including polycaprolactone-b-polyethylene glycol-b-polycaprolactone triblock copolymers of varying sizes. Other building blocks for useful diols include, without limitation glycolides (e.g. polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In additional examples, the polymer composition may include polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and also is stiffer. TPA scaffolds structures are made essentially in the manned described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, Poly(DTE-co-27.5 DT succinate) is used. TPAs and methods of making TPAs are described, for example, in U.S. Pat. No. 5,216,115 and United States Patent Publication No. 2011/0082545, each of which is incorporated herein by reference for its technical disclosure, disclose useful TPAs. Additional references disclosing TPA compositions and methods of making and using those compositions include: Fiordeliso, J, et al., Design, synthesis, and preliminary characterization of tyrosine-containing polyarylates: new biomaterials for medical applications, *J Biomater Sci Polym Ed.* 1994; 5(6):497-510; Huang, X et al., A library of L-tyrosine-derived biodegradable polyarylates for potential biomaterial applications, part I: synthesis, characterization and accelerated hydrolytic degradation *J Biomater Sci Polym Ed.* 2009; 20(7-8):935-55; and Bourke, S L et al., Polymers derived from the amino acid L-tyrosine: polycarbonates, polyarylates and copolymers with poly(ethylene glycol) *Adv Drug Deliv Rev.* 2003 April 25; 55(4):447-66.

In another example, at least one therapeutic agent is added to the scaffold or composition described herein before it is implanted in the patient or otherwise administered to the patient. Generally, the therapeutic agents include any substance that can be coated on, embedded into, absorbed into, adsorbed to, or otherwise attached to or incorporated onto or into the structure or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another example, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting examples, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), Human Vascular Endothelial Growth Factor-165 ($hVEGF_{165}$), Vascular endothelial growth factor A (VEGF-A), Vascular endothelial growth factor B (VEGF-B) hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting examples, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting examples, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin; nitro-fatty acids, such as nitro-oleic acid or nitro-conjugated linoleic acid. Other drugs that may promote wound healing and/or tissue regeneration may also be included.

Structures described herein are preferably made by electrospinning of the biodegradable, elastomeric polymer, and concurrent deposition of the ECM gel, and/or where appropriate a blood product or other liquid, by spraying, e.g., electrospraying. Other compounds or components may be incorporated into a structure as described herein by any method, including absorption, adsorption, mixing, etc.

The deposited biodegradable, elastomeric polymer typically is porous. As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting examples, the porosity of the structure is at least 60%, 65%, 70%, 75%, 80%, 85%, or 90%, or increments therebetween. In another non-limiting example, the average pore size of the structure is between 0.1 and 300 microns, 0.1 and 100 microns, 1-25 microns, including increments therebetween. For example and without limitation, a structure that acts as a barrier to bacteria and other pathogens may have an average pore size of less than 0.5 microns or less than 0.2 microns. In one example, the structures described herein are manufactured by electrospinning. It therefore is often advantageous to adjust the pore size or degree of porosity by varying the polymer concentration of the electrospinning solution or by varying the spinning distance from the nozzle to the target. For example and without limitation, the average pore size may be increased by increasing the amount of polymeric components within the suspension used for electrospinning, which results in larger fiber diameters and therefore larger pore sizes. In another non-limiting example, the average pore size can be increased by increasing spinning distance from the nozzle to the target, which results in less adherence between fibers and a looser matrix. Where ECM gel is co-deposited during the electrospinning, many of the pores (that is a large percentage of the pores or interstices) in the deposited polymer are filled with the ECM gel.

In certain aspects, electrospinning is used to deposit the biodegradable, elastomeric polymer and optionally the ECM gel and/or other liquid, such as a mammalian blood product, media buffer solution, medium, drug products, etc. In its simplest sense, electrospinning is caused by the deposit of a liquid composition, such as polymer fibers onto a target surface caused by an electric potential. Electrospinning methods are well-known in the field of tissue engineering and are conducted essentially as described below. Electrospinning permits fabrication of structures that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy, or structures having varying anisotropy at different parts of the structure. These aligned structures can influence cellular growth, morphology and ECM production. For example, Xu et al. found smooth muscle cell (SMC) alignment with poly(L-lactide-co-ε-caprolactone) fibers. See Xu C. Y., et al., Aligned biodegradable nanofibrous structure: a potential for blood vessel engineering, Biomaterials 2004 (25) 877-86. Lee et al. submitted aligned non-biodegradable polyurethane to mechanical stimulation and found cells cultured on aligned scaffolds produced more ECM than those on randomly organized scaffolds. See Lee C. H., et al., Nanofiber alignment and direction of mechanical strain affect the ECM production of human ACL fibroblast, Biomaterials 2005 (26) 1261-1270.

The process of electrospinning involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically-shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target. Under certain conditions, for instance with solutions lacking sufficient viscosity and/or electrospun with certain tolerances, a fiber is not formed, but a spray is formed, depositing discrete droplets onto the target instead of a fiber. This is electrospraying.

The properties of the electrospun structures, e.g., elastomeric scaffolds, can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting examples, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting examples, the biased target is moved randomly relative to the orifice, so that the resistance to strain in the plane of the non-woven mesh is isotropic. The target can also be electrospun on a rotating mandrel. In this case, the properties of the non-woven mesh may be changed by varying the speed of rotation. The properties of the electrospun structure may also be varied by changing the magnitude of the voltages applied to the electrospinning system. In one non-limiting example, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. Other electrospinning conditions that can be varied include, for example and without limitation, the feed rate of the polymer solutions, the solution concentrations, the polymer molecular weight, the injectors—mandrel gap distance, as well as the injectors—mandrel relative trajectories via CNN control systems.

In further detail and with regard to rotating mandrels, an anisotropic matrix, that is a matrix or article in which at least a portion of which is anisotropic, is prepared by electrospinning on a mandrel, by biasing fiber deposition away from a random, isotropic orientation, resulting in a non-random bias of fiber orientation in a specific orientation, for example with a circumferential bias (at least a portion of deposited fibers are non-randomly oriented in a circumferential direction, resulting in anisotropy), or a longitudinal bias (at least a portion of deposited fibers are non-randomly oriented in a longitudinal direction, resulting in anisotropy). Fiber bias can be introduced in an electrodeposited article by relative movement of the target and the polymer source (e.g., reservoir orifice, needle, pipette tip, etc.). For example, a mandrel target can be rotated at different speeds to generate different degrees of circumferential bias. The mandrel target and/or polymer sources, can be moved, e.g., reciprocated, in a longitudinal direction at different speeds (cycles) and amplitudes while electrospinning to produce varying degrees of longitudinal bias. For example, as shown in. FIG. 10B, for the system depicted, a rotational velocity of 1.5 m/s generates an anisotropy ratio (AR, a common metric for mechanical anisotropy defined as the ratio between the mechanical strain of the most compliant axis divided by the mechanical strain of the stiffer axis) that matches native anisotropy. Rotational speed of the mandrel, and longitudinal movement of the mandrel and/or polymer source can readily be controlled by computer by a person of ordinary skill in the art.

One measure of fiber orientation is referred to as a fiber orientation index. Orientation index is defined in D'Amore et al., "Characterization of the complete fiber network topology of planar fibrous tissues and scaffolds" *Biomaterials* 31 (20), 5345-5354 (2010). Orientation index can be obtained from the average over all fiber segments of $\cos^2(\theta)$ (COS OI), where $\theta$ represents the angle between a fiber segment and the direction of supposed alignment. The anisotropic portions of the matrices described herein have an orientation index ranging from 0.5 to 0.8

In certain examples, electrospinning is performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, use of a mandrel or a revolving disk as a target is contemplated.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In one non-limiting example, the structure is produced by co-electrospinning a polymer suspension comprising a synthetic polymeric component and a biological polymeric component, along with electrospraying the ECM gel and/or other liquid. In another non-limiting example, the polymeric component of the structure is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

If present, an ECM gel component of the structure is sprayed (e.g. pressure sprayed) or electrosprayed concurrently with the electrospinning of the polymer(s). Likewise, the liquid component of the wet-electrospun layer(s) is sprayed or electrosprayed concurrently with the polymeric constituents.

A prosthetic heart valve generally comprises two portions. A first support portion, is annular (forming a ring, but not necessarily defining any particular geometric shape such as a circle or cylinder, and is provided as a point of attachment of the heart valve, for instance, providing a suturing and anchoring structure, as well as an aperture for blood flow through the prosthetic valve. The second portion comprises two or more flexible leaflets that are movable relative to the support portion between an open configuration in which the leaflet permits blood flow through the aperture in a first direction, and a closed configuration in which the leaflet restricts blood flow through the aperture in a second direction opposite the first. The leaflets are joined with adjacent leaflets at a portion of their edges immediately adjacent to the support portion to form a commissure, and are not joined at a portion distal to the support portion, to permit blood to flow through the valve when it is open. When the valve is closed, the leaflets are concave, meaning that the concavity extends towards a central axis of the aperture of the support portion, and the leaflets contact or coaptate with adjacent leaflets to form a seal. Unless indicated otherwise, in reference to the mandrel and heart-valve structures described herein, concave means curved or extending towards the rotational, longitudinal, or central axis, and convex, means curved or extending outwards away from the rotational, longitudinal, or central axis.

FIGS. 1A-1F depict different views of one example of a mandrel useful for preparation of a tricuspid valve prosthesis, as described herein. In reference to FIG. 1A, a mandrel 10 is provided that is useful for the preparation of a tricuspid valve prosthesis by electrospinning. In FIG. 1A, the mandrel 10 has non-conductive and conductive surfaces and, as shown in the exploded view of FIG. 1B, comprises a non-conductive sheath 20, a conductive insert 30, a conductive rod 40 that is electrically-connected to the insert 30, and a conductive, removable axial piece 50 electrically-connected to the rod 40. The rotational axis is shown as a dotted line in FIG. 1B. Elements of the mandrel 10 are disposed about a rotational axis of the mandrel. FIG. 1B is an exploded view of mandrel 10, showing individual elements of mandrel 10. Mandrel 10 has a rotational or longitudinal axis, and a radial direction or radius is normal to any point on the rotational axis. A radius of the mandrel 10 is measured perpendicularly from the rotational axis. A longitudinal direction is in a direction parallel to the longitudinal axis. A circumference of the mandrel is a boundary of circle perpendicular to the longitudinal axis with its center at the longitudinal axis, and a circumferential direction is a direction along the circumference of the circle.

In reference to FIGS. 1B through 1F, non-conductive sheath 20 includes a shaft portion 21, a cylindrical portion 22 having a radius, and longitudinal protuberances 23 extending longitudinally from the cylindrical portion 22. The longitudinal protuberances 23 taper in circumferential width from their attachment to the cylindrical portion 22 to their tips 24. The longitudinal protuberances 23 are inwardly-biased such that their radius decreases from their attachment to the cylindrical portion 22 to their tips. The decrease of radius due to the inward bias is no more that 10% of the radius of the cylindrical portion (that is, the radius of the tips 24 is at least 90%, e.g., 91%, 92%, 93%, 94%, 95%, 96%, 97%, 98%, or 99%, of the radius of the cylindrical portion). In one alternate embodiment, the longitudinal protuberances 23 are not inwardly biased. The profile of the radius as the longitudinal protuberances 23 extend from the cylindrical portion 22 to the tips 24 is shown as being curved or arcuate, but can be linear. Protuberances 25 are shown, which mate with holes in cylindrical portion of the insert 30 (not shown) to orient the insert 30 within the sheath 20. Protuberances 25 are depicted, but can have any useful shape or configuration so long as it permits orientation of the insert 30 within the sheath 20, and does not interfere with the function of the mandrel 10 as described herein. Distribution of mass about the rotational axis of the mandrel 10 is preferably symmetrical or substantially symmetrical or balanced. Insert 30 is manufactured from a conductive material, such as a metal. The insert 30 fits within the sheath 20, as depicted in FIG. 1A. The insert 30 comprises a cylindrical portion 31, a first portion 32 and a second portion 33 extending longitudinally from the first portion 32 opposite the cylindrical portion 31. First portion 32 and second portion 33, comprise ridges 34 extending longitudinally from the cylindrical portion 31 and having a radius, slightly less than the inside radius of the longitudinal protuberances 23, such that they contact the inside surface of the longitudinal protuberances 23 of the sheath 20, so that when the insert 30 is inserted into the sheath 20, the longitudinal protuberances 23 of the sheath 20 at least partially cover and insulate the ridges 34 of the insert 30 in the first portion 32 of the insert 30. The ridges 34 in the first portion 32 have a concave arcuate profile, with a radius that decreases no more than 10%, e.g., no more than 1, 2, 3, 4, 5, 6, 7, 8, 9, or 10% of the radius of the cylindrical portion 31 of the insert 30. That is, the radius of the cylindrical portion 31 and the ridges 34 of the insert 30 range from 90% to 100%, 95% to 100%, or 99% to 100%, inclusive of increments therebetween, of the radius of the inside surface of the cylindrical portion 22 of the sheath 20. In one example, the ridges 34 have a radius that is less than a radius of the cylindrical portion 31. The ridges 34 have a peak 35 and in the second portion 33 of the insert 30, the ridges 34 have a decreasing radius from the first portion 32 to the tip 36 of the insert 30, with a concave arcuate profile 37, such as a circular or parabolic profile. The "profile" of the longitudinal protuberances 23 and ridges 34 refers to the longitudinal change of radius of those features, e.g., for the ridges 34, first from the cylindrical portion 31 to the second portion 33 and secondly from the first portion 32 to the tip 35 of the insert 30. Alternately, the ridges 34 of the second portion 33 have a linear profile. The first and second portions 32 and 33 of the insert 30 also comprise curved, concave regions 38 between the ridges 34. Surfaces of adjacent concave regions 38 on opposite sides of the a same ridge 34, of the insert 30 are generally parallel in at least a portion of the second portion 33 of the insert 30. By "generally parallel", it is meant that the surfaces are not necessarily perfectly parallel, and when used as a target for electrodeposition of a polymer composition to produce a prosthetic heart valve, produces coaptating leaflets that contact each-other in a closed position. The shape depicted for the concave regions and depicted leaflets also may be referred to as "leaflet shaped", meaning the geometry of the concave regions mimics that of bicuspid or tricuspid heart valve leaflets.

FIGS. 2A-2D depict different views of one example of a mandrel useful for preparation of a tricuspid valve prosthesis, as described herein. In Reference to FIGS. 2A-2C, a mandrel 110 is provided. The mandrel 110 has a rotational axis essentially as shown for mandrel 10 of FIG. 1B, and comprises similar structures as compared to the mandrel of FIG. 1A, except that it is used to form a prosthetic bicuspid valve, and includes a non-conductive, insulating sheath 120, a conductive insert 130, a conductive rod 140 that is electrically-connected to the insert 130, and a conductive, removable axial piece 150 electrically-connected to the rod 140.

Figure 2B:
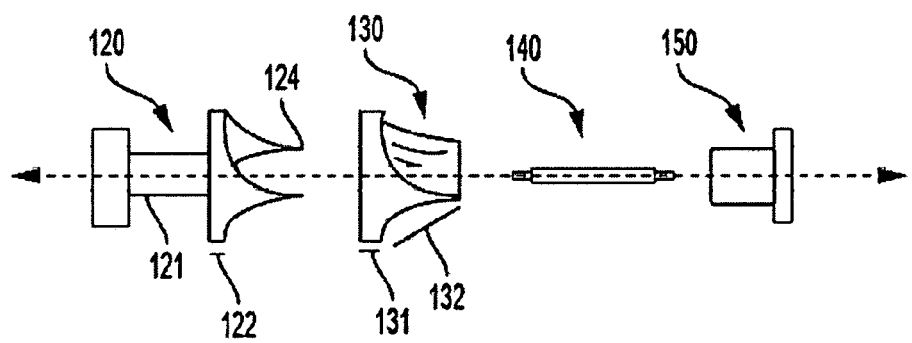
FIG. 2B is an exploded view of the double component mandrel of FIG. 2A.
Figure 2C:
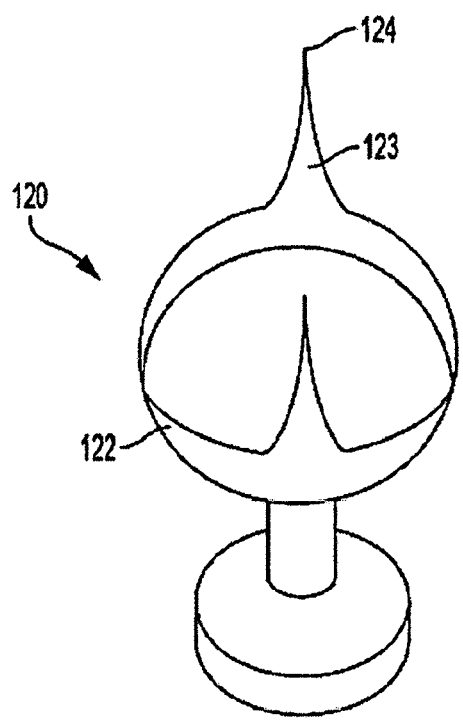
FIG. 2C is a schematic representation of a perspective view of a non-conductive plastic shield of the mandrel of FIG. 2A.
Figure 2D:
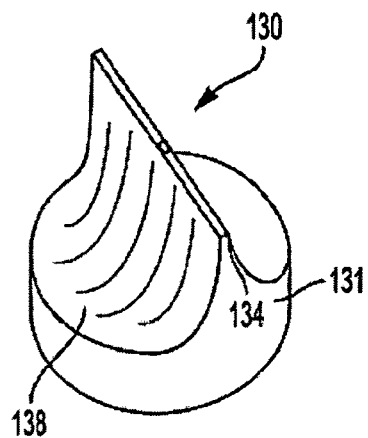
FIG. 2D is a schematic representation of a perspective view of the conductive insert of the mandrel of FIG. 2A.

In reference to FIGS. 2B through 2D, non-conductive sheath 120 includes a shaft portion 121, a cylindrical portion 122 having a radius, and longitudinal protuberances 123 extending longitudinally from the cylindrical portion 122. The longitudinal protuberances 123 taper in circumferential width from their attachment to the cylindrical portion 122 to their tips 124. unlike the mandrel 10 of FIGS. 1A-1F, the longitudinal protuberances 123 are not inwardly-biased. However, in an alternate aspect (not shown, but essentially as shown to the mandrel 10 of FIGS. 1A-1F), the longitudinal protuberances 123 are inwardly-biased, such that their radius decreases from their attachment to the cylindrical portion 122 to their tips. The decrease of radius due to the inward bias is no more that 10% of the radius of the cylindrical portion (that is, the radius of the tips 24 is at least 90%, e.g., 91%, 92%, 93%, 94%, 95%, 96%, 97%, 98%, or 99%, of the radius of the cylindrical portion). When inwardly-biased, the profile of the radius as the longitudinal protuberances 123 extend from the cylindrical portion 122 to the tips 124 may be curved or arcuate, or linear. Protuberances that which mate with holes in cylindrical portion of the insert 130, to align the sheath 120 with insert 130 are not shown, but are as described in relation to FIG. 1C. Distribution of mass about the rotational axis of the mandrel 110 is preferably symmetrical or substantially symmetrical or balanced. Insert 130 is manufactured from a conductive material, such as a metal. The insert 130 fits within the sheath 120, as depicted in FIG. 2A. The insert 130 comprises a cylindrical portion 131, and a first portion 132 extending longitudinally from the cylindrical portion 131. First portion 132 comprises ridges 134 extending longitudinally from the cylindrical portion 131 and having a radius, slightly less than the inside radius of the longitudinal protuberances 123, such that they contact the inside surface of the longitudinal protuberances 123 of the sheath 120, so that when the insert 130 is inserted into the sheath 120, the longitudinal protuberances 123 of the sheath 120 at least partially cover and insulate the ridges 134 of the insert 130 in the first portion 132 of the insert 130. The ridges 134 in the first portion 132 are depicted as linear with the same radius as the cylindrical portion 131, but, as with the mandrel 10 of FIG. 1A, alternatively may be inwardly biased, and have a concave arcuate profile, with a radius that decreases no more than 10%, e.g., no more than 1, 2, 3, 4, 5, 6, 7, 8, 9, or 10% of the radius of the cylindrical portion 131 of the insert 130. That is, the radius of the cylindrical portion 131 and the ridges 134 of the insert 130 range from 90% to 100%, 95% to 100%, or 99% to 100%, inclusive of increments therebetween, of the radius of the inside surface of the cylindrical portion 122 of the sheath 120. In one example, the ridges 134 have a radius that is less than a radius of the cylindrical portion 131. As above, the "profile" of the longitudinal protuberances 123 and ridges 134 refers to the longitudinal change of radius of those features, e.g., for the ridges 134, as they extend from longitudinally from the cylindrical portion 131. The first portions 132 of the insert 130 also comprise curved, concave regions 138 between the ridges 134. Surfaces of adjacent concave regions 138 on opposite sides of the a same ridge 134, of the insert 130 are generally parallel distal to the cylindrical portion, such that when used as a target for electrodeposition of a polymer composition to produce a prosthetic heart valve, the target produces coaptating leaflets that contact each-other in a closed position. As above, the shape depicted for the concave regions and depicted leaflets also may be referred to as "leaflet shaped", meaning the geometry of the concave regions mimics that of bicuspid or tricuspid heart valve leaflets.

In one aspect, the first portion of the electrodeposition target has a radius substantially the same as the cylindrical portion. In one aspect, the electrodeposition target includes ridges that are spaced symmetrically about the rotational axis.

Figure 2E:
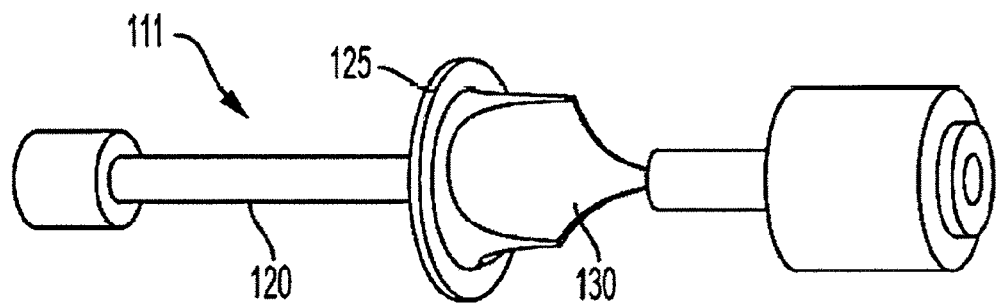
FIGS. 2E-2G are schematic representations of variations of the mandrel of FIGS. 1A and 2A.
Figure 2F:
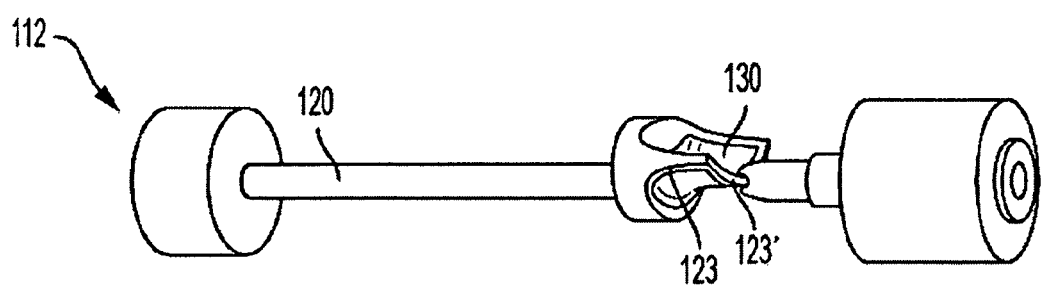
Figure 2G:
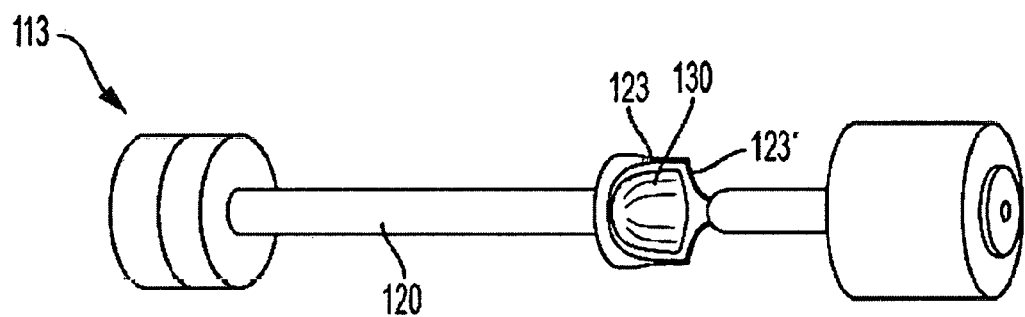
Figure 2J:
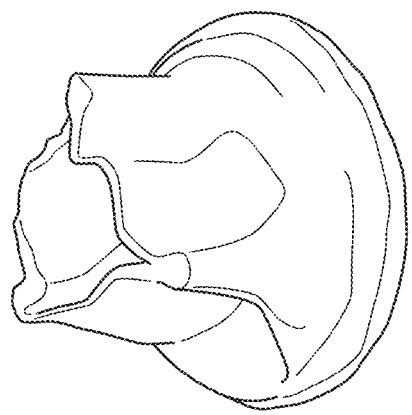
FIG. 2J is a photograph of a prosthetic tricuspid valve produced on a mandrel according to FIG. 2E, including a sewing ring.
Figure 2I:
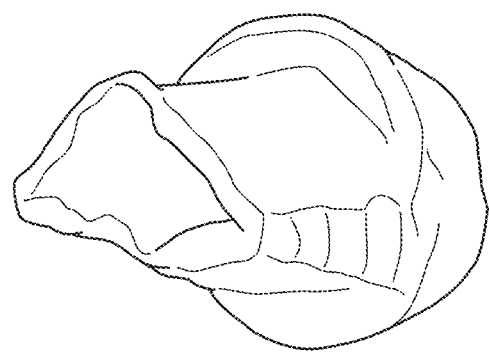
FIGS. 2H and 2I are photographs of a prosthetic mitral valve produced on a mandrel essentially as shown in FIG. 2F.
Figure 2H:
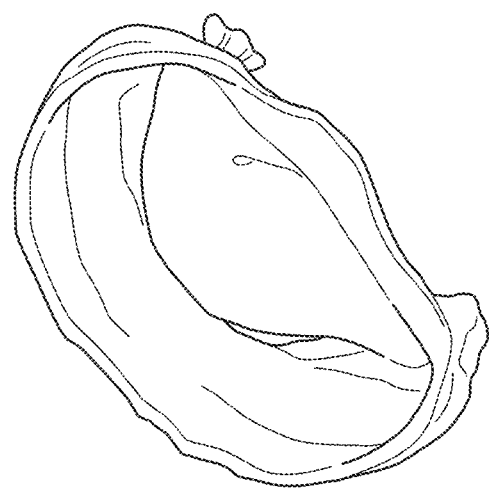

FIGS. 2E-2G depict alternate aspects of the mandrel described herein. FIG. 2E shows a mandrel 111 essentially as shown in FIG. 1A (certain reference numerals omitted for clarity), having a sheath 120, and a radially-extending sewing ring 125 about the cylindrical portion. A radially-extending sewing ring may be included in any mandrel design described herein, to provide additional material in the resultant polymer matrix valve structure prepared on the mandrel. The radially-extending sewing ring, shown extending perpendicularly to the longitudinal axis need not extend perpendicular to the longitudinal axis. FIG. 2F depicts a variation on the mandrel of FIG. 2A for preparation of a bicuspid valve. The mandrel 112 is essentially as shown in FIG. 2A (certain reference numerals omitted for clarity), including a non-conductive sheath 120 and an insert 130, but the first portion of the insert 130 is radially curved, and the sheath 120 includes longitudinal protuberances 123 over the periphery of the first portion, including over the distal edge 123' of the insert. FIG. 2G depicts essentially the same structure as in FIG. 1A (certain reference numerals omitted for clarity), including a non-conductive sheath 120, but smaller in size, and the longitudinal protuberances 123 cover the entire ridges of the insert, including the ridges 123' of the second portion. FIGS. 2H and 2I show bottom and top sides of a bicuspid valve produced on a mandrel according to FIG. 2F. FIG. 2J is a photograph of a tricuspid valve produced on a mandrel according to FIG. 2E, including a sewing ring.

The mandrel structures depicted in FIGS. 1A-1F and 2A-2G are merely exemplary. The mandrel can have any useful shape, and construction, for example, the mandrel can be manufactured from a unitary conductive material, with non-conductive coating deposited on portions thereof to produce the same pattern, or a similar pattern to the pattern produced by the assemblies shown in FIGS. 1A-1F and 2A-2G.

A prosthetic heart valve is prepared by electrodeposition of polymer fibers on a mandrel, as described herein. The resulting structure is removed from the mandrel, and is trimmed as necessary to ensure that an aperture is formed between the leaflets, and the commissure is only of a desired length, to produce properly coaptating leaflets. The matrix produced by electrospinning preferentially has a thickness of from 100 μm to 400 μm. The diameter of the cylindrical portion is that of a native heart valve, and as one of ordinary skill can appreciate, can be varied, by varying the radius of the cylindrical portion of the mandrel. Similarly, AR can be varied covering the full range of ARs measured or estimated for pig and human valves AR=1-3, corresponding stress and strain values 1 span from 0-500 kPa and 0-40% strain respectively. Finally, native tissue bending elastic modulus range (1000-20000) kPa can be covered as well by changing the rastering (mandrel linear motion) velocity.

Figure 3:
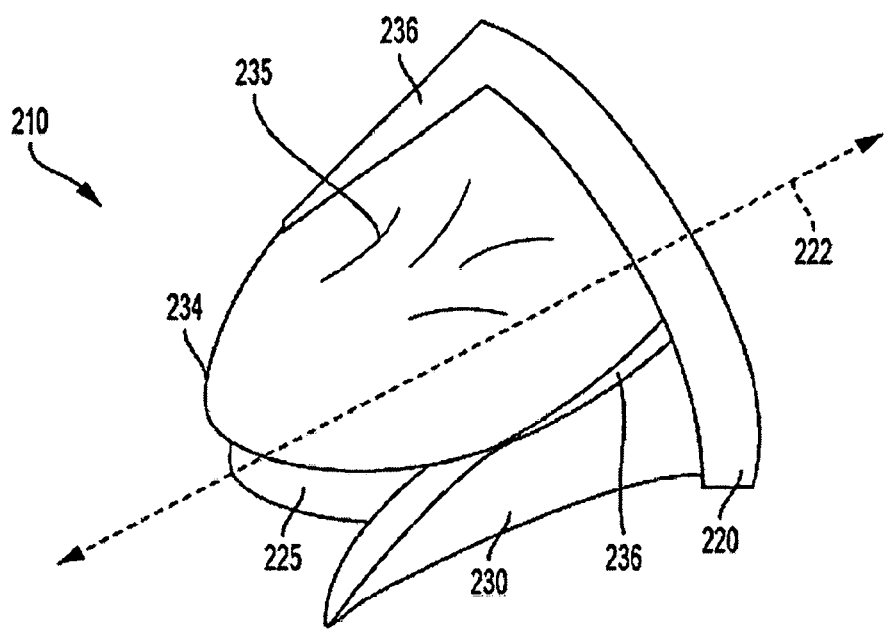
FIG. 3 is a schematic representation of a perspective view of an engineered tricuspid valve made with the mandrel of FIG. 1A.
Figure 4C:
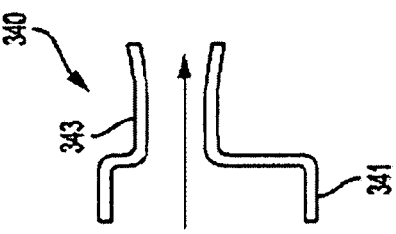
FIGS. 4B and 4C are schematic representations of an engineered bicuspid valve made with the mandrel of FIG. 2A when the valve is in a closed position.
Figure 4E:
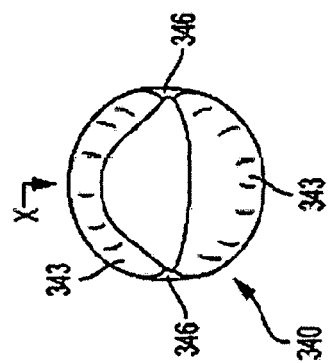
FIGS. 4D and 4E are schematic representations of an engineered bicuspid valve made with the mandrel of FIG. 2A when the valve is in an open position.
Figure 4B:
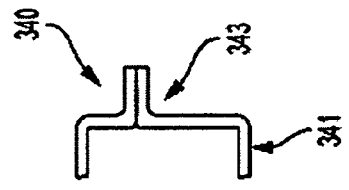
Figure 4D:
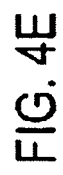
Figure 4A:
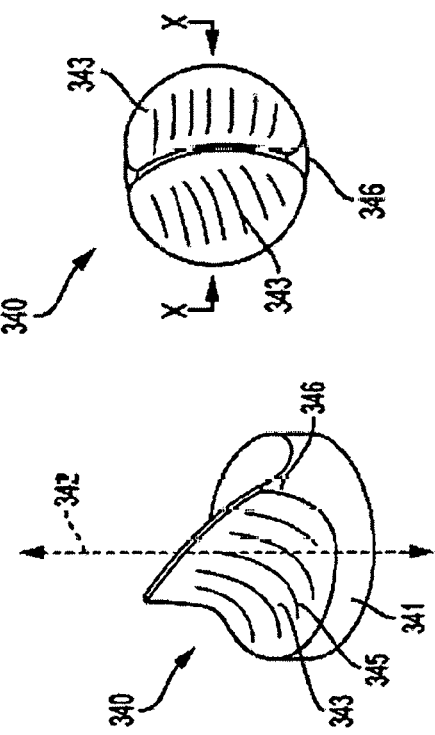
FIG. 4A is a schematic representation of a perspective view of an engineered bicuspid valve made with the mandrel of FIG. 2A.

In another aspect, a prosthetic tricuspid valve 210 is shown in FIG. 3. The valve 210 comprises a support portion 220 defining a longitudinal axis 222 and an aperture 225 passing through the valve 210; and three concave leaflets 230 extending longitudinally from a distal end 234 of the support portion 220, wherein each leaflet 230 comprises a concave belly or central region 235 and a commissure 236 joining adjacent leaflets 230. The fiber matrix at the central region 235 and commissures 236 is anisotropic, with different fiber orientations at the central region 235 and commissures 236, with the fiber orientation at the central region 235 being more circumferential than at the commissures 236.

k another aspect, a bicuspid valve 340 is provided a shown in FIGS. 4A-4E. The valve 340 is formed from a matrix of fibers and comprises a support portion 341 defining a longitudinal axis 342 and an aperture; and two concave leaflets 343 extending longitudinally from the support portion 341, wherein each leaflet portion comprises a central region 335 and commissures 346, joining the leaflets. FIGS. 4B and 4D provide a top view of the bicuspid valve 340 along the longitudinal axis in a closed and open position, respectively. FIGS. 4C and 4E depict the valve 340 along X in corresponding FIGS. 4B and 4D. FIGS. 4B and 4C depict the valve 340 in a closed configuration, and FIGS. 4D and 4E depict the valve in an open configuration where blood flows in the direction of the arrow. Note that the bicuspid valve leaflets have a radially-curved profile, with one leaflet larger than the other.

In any aspect of the valve structures described herein, the identification of a cylindrical portion is merely illustrative and exemplary of one possible geometry of potential support structures (e.g. support portions) for the leaflets. In practice, and in alternate embodiments, the support structure can take on any useful shape, so long as it can support the leaflet function, and anchor the valve in place, for example by serving at least in part as a sewing ring, or providing an attached sewing ring, for suturing the structure in place during implantation, and/or for attachment to additional support or placement structures. cylindrical shape may be considered the simplest, and most appropriate geometry for purposes herein. The leaflet portions of the valves depicted in FIGS. 3 and 4A-4E are flexible and concave, and, when in a closed configuration or position, are in contact with (coaptate) adjacent leaflets distal to the cylindrical or support portion of the prosthetic valve to prevent blood backflow. When in an open configuration, the leaflets extend the aperture of the (e.g., cylindrical) support structure, permitting blood flow through the device. Of note is that for any valve structure, and for corresponding mandrel target shapes, the leaflets do not have to be symmetrical in size, as with native mitral and tricuspid valves. In any instance, the target shape for the mandrel, in reference to the concave leaflet shape of the insert, the shape can be referred to as a leaflet shape, such as a mitral, tricuspid, aortic, or pulmonary valve leaflet-shape, or a pathological mitral, tricuspid, aortic, or pulmonary valve leaflet-shape, referring to native or damaged/pathological shapes of leaflets or cusps of valves of an organism, such as a human, or a mammal. Pathological shapes find use in research, studying defects in valve structures. Table 1 provides exemplary diameters for heart valves, and therefore for mandrel target diameters for electrospinning. The values of Table 1 are appropriate for humans, pigs, and other animals >40 kg. For animals less than 40 kg, such as minipigs, sheep and goats, the diameters should be, e.g., 30% smaller. For even smaller animals, such as rabbits and rats, the values should be, e.g., 90% smaller.

TABLE 1

|  | aortic or pulmonary (all cusps are the same size) | mitral | Tricuspid (one cusp bigger than the other two) |
|---|---|---|---|
| Small size | 17 mm | 24 mm | 26 mm |
| Medium size | 20 mm | 30 mm | 30 mm |
| Large size | 23 mm | 34 mm | 34 mm |

By electrodepositing polymer fibers on the mandrel structures described herein, while anisotropy can be imparted to all or portions of the prosthetic heart valve structure the main direction of alignment of the fibers can be varied within the same engineered valve. In contrast, conventional deposition targets such as rotating mandrels or flat surfaces will produce materials with either no alignment or constant direction of alignment within the same construct. This aspect is particularly relevant because native valve leaflets are characterized by a constant level (AR) of fiber alignment within the leaflet, but also by a main direction of alignment that changes within the same leaflet. For example, while native leaflet belly region is oriented circumferentially the commissure regions are oriented almost longitudinally. Precise fiber deposition on a concave surface allows for re-creating the same effect with rotating the main direction of alignment of scaffold fibers from the belly region to the commissures. As such, the mandrels described herein, and methods of using the mandrels provides precise control of device thickness, device size, device shape, anisotropy, elastic modulus in bending, and allows for curvilinear fibers as opposed to straight or isotropic alignment.

In another aspect, the fibers are at least partially deposited and aligned in a circumferential direction in at least one portion of the heart valve, for example in the concave portions, or bellies of the leaflets. In yet another aspect, the fibers are aligned in at least one portion of the valve in a non-directional or isotropic pattern—for example in portions between the bellies of the leaflets and the commissures.

The prosthetic heart valves are produced by electrodeposition of one or more bioerodable, biocompatible polymer compositions. Examples of useful polymer compositions include one or more of poly(ester urethane) urea (PEUU), poly(ether ester urethane)urea (PEEUU), poly(ester carbonate)urethane urea (PECUU), poly(carbonate)urethane urea (PCUU), a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polyurethane, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin.

In yet another aspect, a method of making a prosthetic heart valve structure is provided, along with the product of the method, the method comprising electrodepositing a biodegradable, biocompatible polymer composition onto an electrodeposition target, e.g., a mandrel, described herein. In another aspect of the method thereof, the polymer composition comprises a synthetic polymer. In another aspect of the method thereof, the synthetic polymer selected from a group consisting of one or more of poly(ester urethane) urea (PEUU), poly(ether ester urethane)urea (PEEUU), poly(ester carbonate)urethane urea (PECUU), poly(carbonate)urethane urea (PCUU), a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polyurethane, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin. In another aspect of the method thereof, the synthetic polymer is a PEUU, PEEUU, PECUU or PCUU. In another aspect of the method thereof, the anisotropy of the electrodeposited polymer composition is oriented in at least one portion of the structure, thereby producing anisotropic portions in the structure. In another aspect of the method thereof, fibers, e.g., more than 50% of electrodeposited polymer, are oriented in a circumferential direction within the concave central portion or bellies of the at least two leaflet portions and/or wherein fibers, e.g., more than 50% of electrodeposited polymer, are oriented in a longitudinal direction at or immediately adjacent to commissures between the at least two concave leaflet portions. In another aspect of the method thereof, the shape and size of the electrodeposition target mimics native anatomy, shape and size to duplicate human or animal's healthy or pathological anatomy, such as valve anatomy. The electrodeposited valve structure is removed from the electrodeposition target, and as necessary, joined leaflet portions are separated, leaving a commissure joining at least a portion of the leaflet portions. The valve structure may be rinsed or hydrated in a suitable solution, such as water, normal saline or PBS. The valve structure is optionally seeded with cells, and optionally incubating the cells on the valve structure so that the cells coat and/or infiltrate at least a portion of the valve structure. In another aspect, the method further comprises electrodepositing, spraying or otherwise adding or incorporating a second polymer composition, an ECM gel, a drug, water, saline, PBS, cell culture medium, cells, biologics, salts, buffers, cytokines, growth factors, or combinations thereof onto the electrodeposition target.

In use, the valve prostheses described herein are implanted in a patient at a site of a native valve, e.g., a valve annulus. In the case of the heart valves, the device is sewn in place at the heart valve annulus, and optionally connected, e.g., via cusps on the prosthetic valve, to papillary muscles for atrio-ventricular valves or the commissures for ventriculo-arterial valves. In one aspect, the valve prostheses is connected to, e.g. sewn into a frame, such as a stent or similar framing structure, as are broadly-known in the art, and are then placed and implanted into the native valve annulus. Suitable frames, for example and without limitation fabricated from shape memory metals, such as Nitinol, or polymers, are broadly-known, and suitable frame configurations can be determined.

EXAMPLES

Example 1

Figure 5:
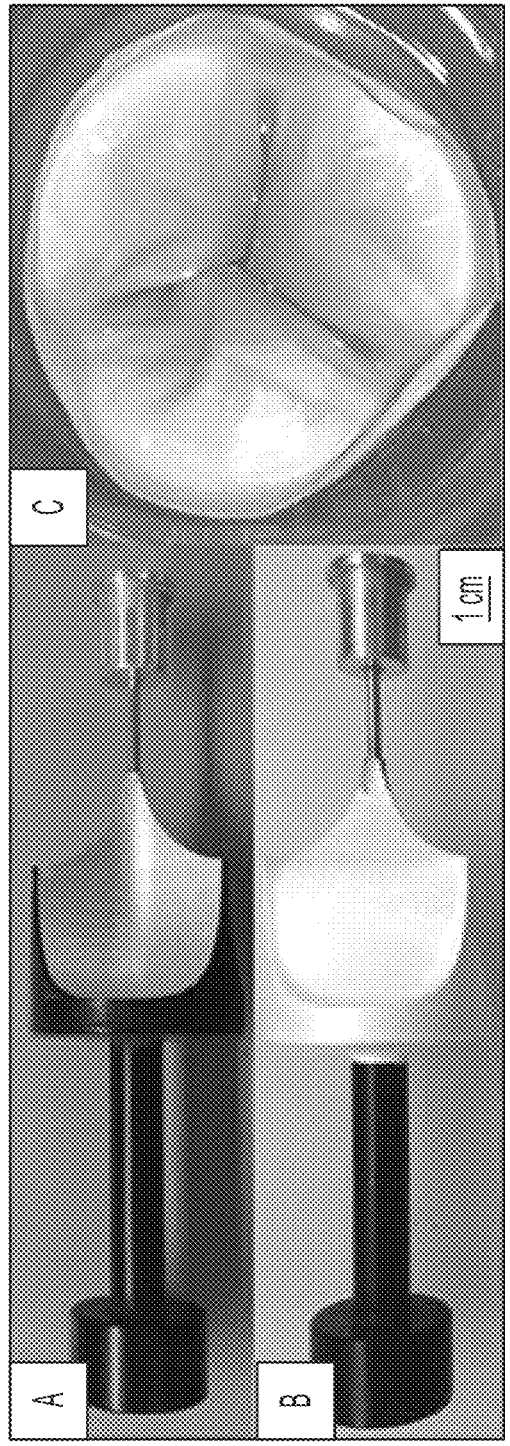
FIG. 5(A-D) illustrates the micro-fibers deposition process.
Figure 5:
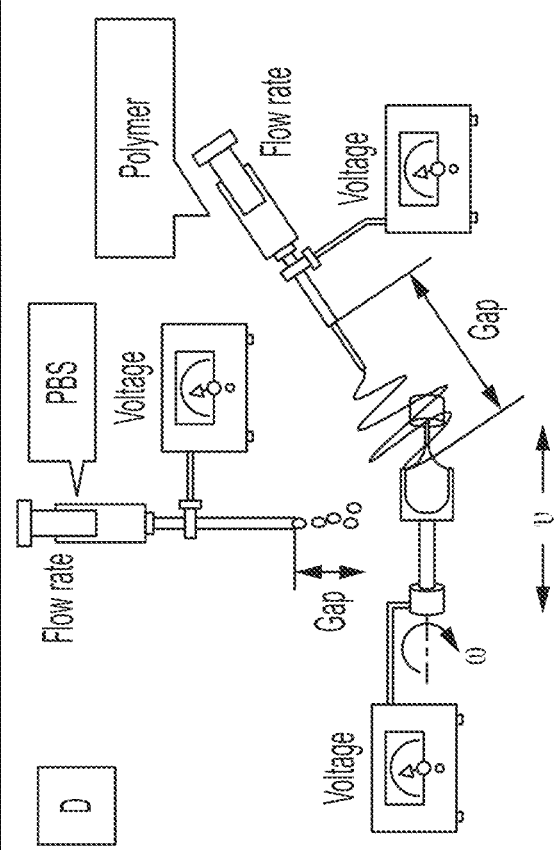

A three-leaflet version of the mandrel design described herein is shown essentially in FIGS. 1A-1F and its use in preparing a tricuspid valve is depicted in FIGS. 5A-5D. FIG. 5A is a photographic image of a double component mandrel before the polymer fibers deposition. As depicted in FIG. 5B, the polymer, which in this case is a PEUU, is electrodeposited for 3 hrs about the conductive portion of the target, with selective deposition of the polymer fibers on the conductive target. Processing conditions for this fabrication were: polymer voltage 11 kV, second stream (PBS) voltage 8 kV, mandrel voltage −5 kV, polymer flow rate 1.5 ml/hr, second stream flow rate 1.2 ml/hr, polymer-mandrel gap 15.5 cm, second stream-mandrel gap 4.5 cm, PEUU solvent weight/volume 12%, humidity<40%, rastering speed 0 cm/s, mandrel speed 372 rpm. As depicted in FIG. 5D, the mandrel is placed in a chuck and is rotated and moved in a longitudinal direction. While in a typical example, the mandrel is rotated, and the electrodeposition nozzles are not rotated about the mandrel, the spatial location and relative orientation of the polymer nozzles and the mandrel can be controlled either manually, or more typically controlled by a computer, using standard robotics and stages. The resulting tricuspid valve is shown in FIG. 5C. The double component design (shield+target) aims to concentrate fibers deposition on the concave zones only. Shapes and size of the parts can be varied based on patient' anatomy. The same concept remains applicable to non-biomedical applications requesting fiber deposition on concave areas.

Example 2

A two-leaflet (bicuspid) version of a mandrel design described herein essentially as shown in FIGS. 2A-2D and 2F, and its use in preparing a bicuspid valve, with fiber deposition essentially as described in Example 1, and a prosthetic bicuspid valve is depicted in FIGS. 4A-4E. Polymer fibers, e.g., PEUU, are deposited essentially as described in Example 1. Similarly, control on anisotropy and elastic modulus are achieved by changing mandrel speed and rastering speed respectively.

Example 3

Example 3 provides qualitative testing of the leaflet coaptation at rest for tricuspid valves prepared using a double component mandrel, as described in Example 1. The trileaflet valve is removed from a mandrel having the three-leaflet design (FIG. 5A) and the valve was immersed in PBS. Qualitative inspection of the valve construct prepared as described in Example 1, when the valve construct was immersed on a liquid, showed leaflet coaptation at rest (FIG. 5B). In contrast, conventional valve leaflets obtained by electrospinning on regular shapes are flat or cylindrical. In the specific case of flat or cylindrical shape mandrel the lack of leaflet concavity as well as the need for structurally connecting the different leaflets does not allow for proper coaptation at rest.

Example 4

Figure 6A:
FIG. 6A is a photographic image of the side view of a trileaflet valve removed from the mandrel.
Figure 6B:
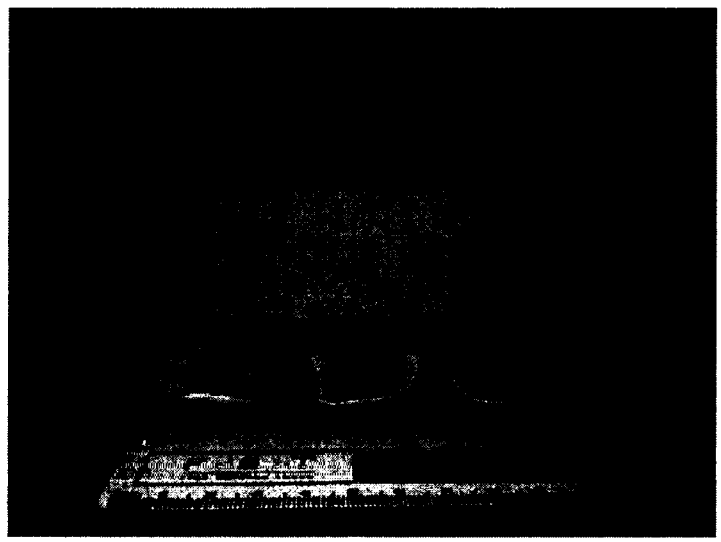
FIG. 6B is a photographic image of dissected leaflets showing concave shape at rest. The process produces leaflets with physiological curvature dictated by the geometry of a double component mandrel described herein.

Example 4 provides further measurement and analysis of the three-dimensional shape of tricuspid valves prepared using a double component mandrel as described in Example 1. The photographs of tricuspid valves prepared as described in Example 1, shown in FIGS. 6A and 6B, illustrate how the valves and the process to make these valves described herein produces tricuspid valves having physiological curvature, which is dictated by the geometry of the mandrel used in preparing them.

Example 5

Figure 7A:
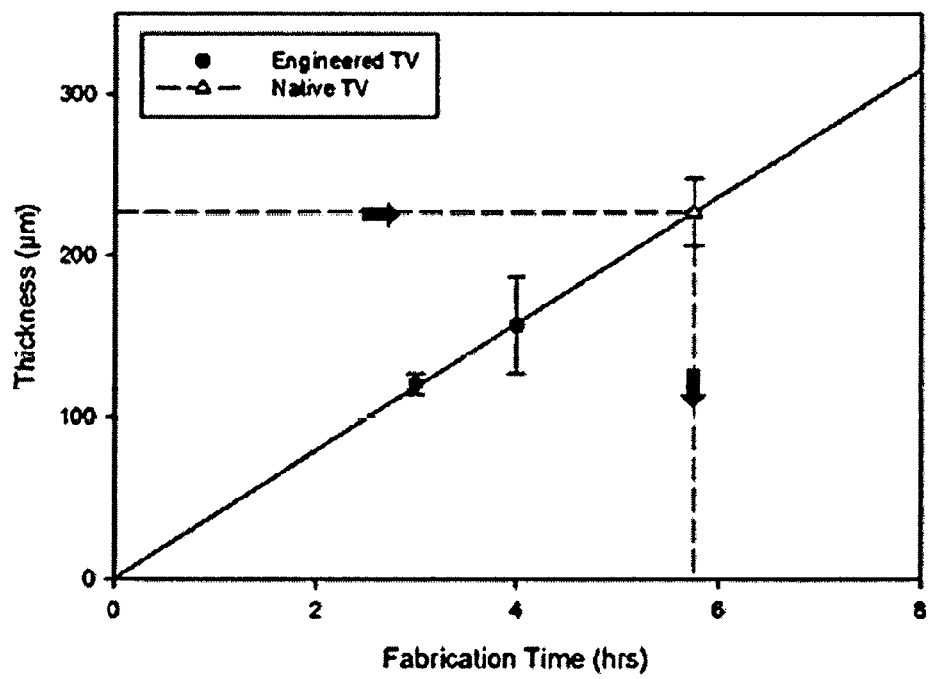
FIG. 7A is graph showing the thickness of an engineered heart valve prepared using the double component mandrel described herein in function of the deposition time (independent fabrications for each data point), and corresponding data point for native porcine tricuspid valve, data are presented as mean±st.e, showing that process scalability in terms of construct thickness by monitoring the leaflets thickness vs. deposition time.

Example 5 provides data comparing thicknesses for leaflet valves prepared using a double component mandrel described herein and native porcine tricuspid valves. The example also shows how thickness is linearly affected by deposition time. Material processing variables were the same utilized in Example 1. A specific thickness of interest can be achieved based on the deposition time. FIG. 7A shows a graph of thickness vs. deposition time for an engineered heart valve and native porcine tricuspid valve (n=3 (3 hours), n=4 (4 hours), n=4 (native porcine tricuspid valve)). The engineered heart valves were made by independent fabrications demonstrating that a specific thickness of interest can be achieved based on the deposition time, e.g. predetermined fabrication times can be set to obtain thickness on the artificial leaflets comparable to native leaflets. FIGS. 7B and 7C show native porcine tricuspid valve and engineered tricuspid valve thickness distributions, respectively, over the leaflet area after 3 hrs of fabrication. The thickness maps comparison (native vs. artificial) illustrates comparable leaflets thickness values over the entire surface.

Example 6

Figure 8:
FIG. 8(A-I) provides representative photographic images of engineered valves for the nine configuration studied changing mandrel tangential velocity V1, V2, and V3 (control on anisotropy) and rastering velocity R0, R1, and R2 (control on bending modulus), showing the feasibility of adopting a mandrel design described herein for different fabrication configurations control over valve leaflets in plane and out of plane mechanics the mandrel design was tested on nine different configuration covering operational range of interest for the valve application (mandrel tangential velocity: 0.3-3 m/s. rastering linear velocity: 0-2.5 cm/s).
Figure 8:
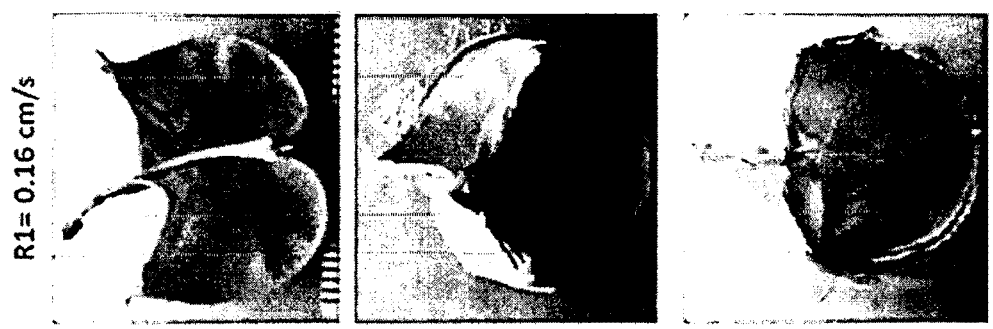
Figure 8:
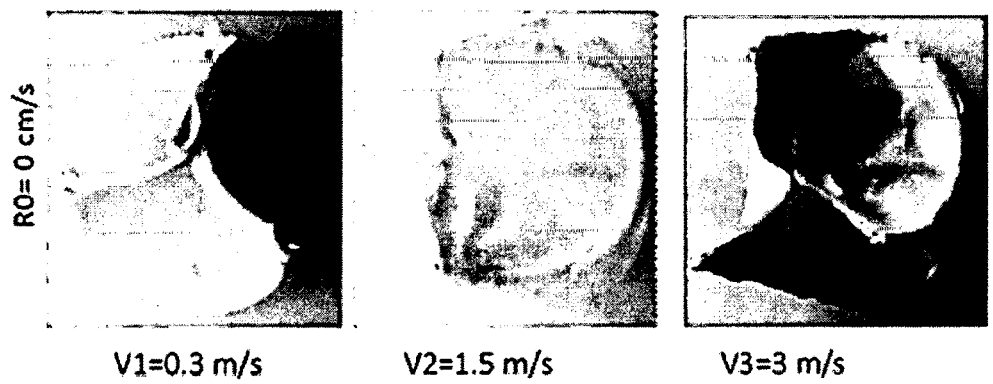

Example 6 provides data related to the leaflet mechanics for the valves prepared using a double component mandrel described herein. In order to prove control over valve leaflets in-plane and out-of-plane mechanics, the mandrel design described herein was tested for nine different conditions, covering operational range of interest for the valve application (mandrel tangential velocity: 0.3-3 m/s. rastering (longitudinal) linear velocity: 0-2.5 cm/s) (see FIG. 8). PEUU was used for these experiments. Results shown in FIGS. 8(A-I) confirmed mandrel velocity directly controls mechanical anisotropy (increasing difference in compliance over the mandrel longitudinal direction for V1, V2, V3). In contrast, the rastering velocity did not affect significantly the level of anisotropy (non-significant differences between circumferential and longitudinal direction for R0, R1, R2). Representative images of valve constructs demonstrated the feasibility of adopting the presented mandrel design for different fabrication configurations.

Example 7

Figure 9A:
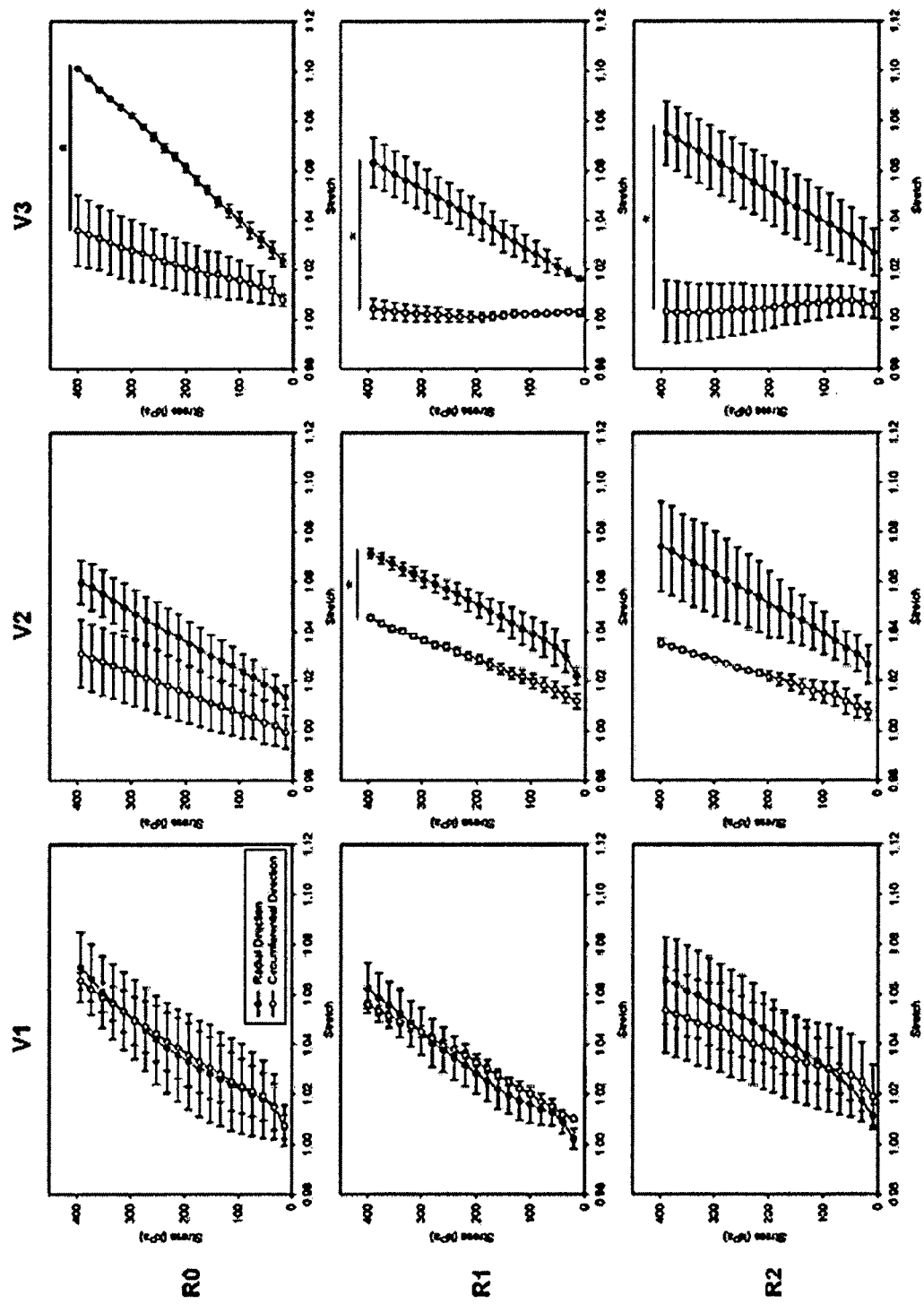
FIG. 9A are graphs showing engineered valves in-plane mechanical responses tested with biaxial tensile test in equi-stress mode for nine configurations obtained by changing mandrel tangential velocity (ω, control on anisotropy) and rastering velocity (ν, control on bending modulus), n=3 mean±st.e.
Figure 9B:
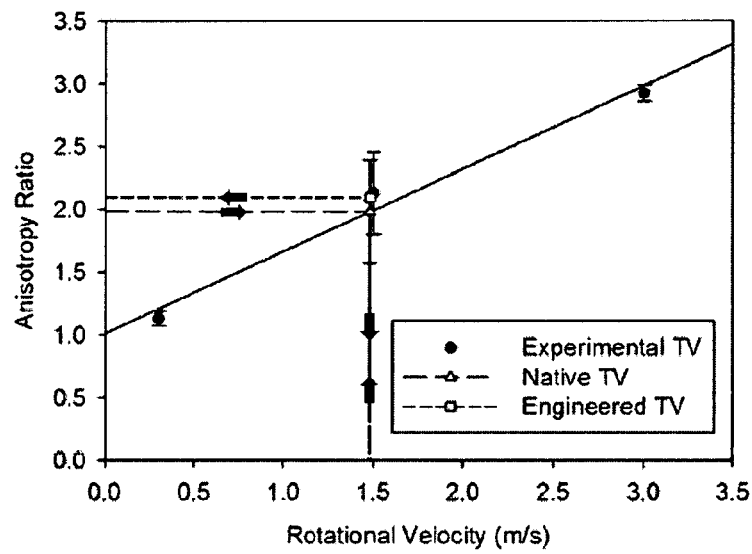
FIG. 9B is a graph showing the anisotropy ratio (AR) defined as the mechanical strain ratio between the longitudinal and circumferential directions has been utilized as metric for anisotropy, AR vs. rotational velocity summarizes the results in FIG. 9A showing the AR for the valve configurations in FIG. 9A as well as the native porcine tricuspid valve value. Proper mandrel velocity necessary to fabricate a tricuspid valve with native mechanics (~1.5 m/s) has been identified by linear interpolation of the ARs at 0.3, 1.5, 3 [m/s].
Figure 9C:
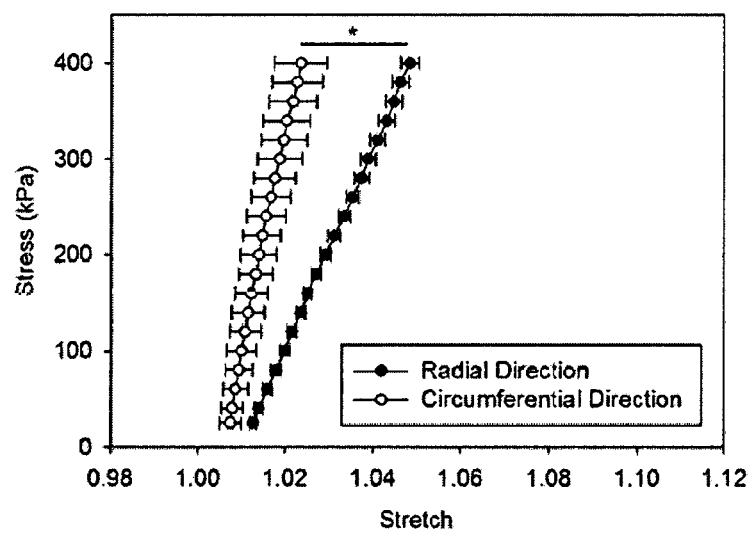
FIG. 9C is a graph showing the biaxial response of engineered tricuspid valve duplicating AR of porcine native tricuspid valve (radial direction of the valve=longitudinal direction of the mandrel, circumferential direction of the valve leaflet=circumferential direction of the mandrel), using data produced with a custom made biological tissue biaxial testing device and protocols previously described in "Biaxial Mechanical Evaluation of Planar Biological Materials" by M. Sacks in Journal of elasticity and the physical science of solids, 07-2000, Vol. 61, Issues 1-3, pp 199-246. Tests were conducted at room temperature, under quasi-static conditions, and samples were continuously immersed in PBS during the test, equistress biaxial protocol with peak 400 kPa was adopted, after pre-conditioning free float state was utilized as reference configuration.

Example 7 provides testing results related to the mechanic responses of leaflet valves prepared using a double component mandrel described herein as compared with native porcine tricuspid valves when varying mandrel tangential velocity and rastering velocity. Processing conditions for these fabrications were: polymer voltage 11 kV, second stream (PBS) voltage 8 kV, mandrel voltage −5 kV, polymer flow rate 1.5 ml/hr, second stream flow rate 1.2 ml/hr, polymer-mandrel gap 15.5 cm, second stream-mandrel gap 4.5 cm, PEUU solvent weight/volume rate %, humidity<40%, rastering speed were 0, 0.16 and 2.5 cm/s whereas mandrel tangential velocities were 0.3, 1.5 and 3 m/s. FIG. 9A are graphs showing engineered valves in-plane mechanical responses tested with biaxial tensile test in equi-stress mode for nine configurations obtained by changing mandrel tangential velocity (ω, control on anisotropy) and rastering velocity (v, control on bending modulus), n=3 mean±st.e. FIG. 9B is a graph showing the anisotropy ratio (AR) defined as the mechanical strain ratio between the longitudinal and circumferential directions has been utilized as metric for anisotropy, AR vs. rotational velocity summarizes the results in FIG. 9A showing the AR for the valve configurations in FIG. 9A as well as the native porcine tricuspid valve value. Proper mandrel velocity necessary to fabricate a tricuspid valve with native mechanics (~1.5 m/s) has been identified by linear interpolation of the ARs at 0.3, 1.5, 3 [m/s]. FIG. 9C shows a graph showing the biaxial response of engineered tricuspid valve duplicating AR of porcine native tricuspid valve (radial direction of the valve=longitudinal direction of the mandrel, circumferential direction of the valve leaflet=circumferential direction of the mandrel), using data produced with a custom made biological tissue biaxial testing device and protocols previously described in "Biaxial Mechanical Evaluation of Planar Biological Materials" by M. Sacks in Journal of elasticity and the physical science of solids, 07-2000, Vol. 61, Issues 1-3, pp 199-246. Tests were conducted at room temperature, under quasi-static conditions, and samples were continuously immersed in PBS during the test, equistress biaxial protocol with peak 400 kPa was adopted, after pre-conditioning free float state was utilized as reference configuration.

Example 8

Figure 10:
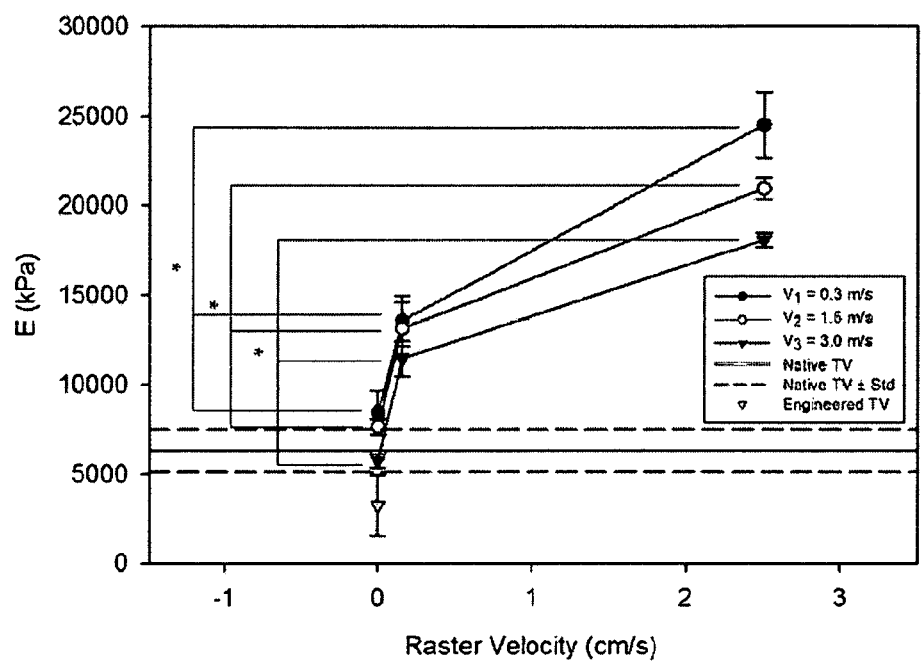
FIG. 10 is a graph showing the leaflet bending modulus for different values of mandrel tangential velocities (0.3, 1.5, 3 [m/s]) and rastering velocities (0, 0.25, 2.5 [cm/s]) n=3 mean±st.e.

Example 8 provides additional testing results related to the mechanic responses of leaflet valves prepared using a double component mandrel described herein as compared with native porcine tricuspid valves when varying mandrel tangential velocity and rastering velocity. More specifically, the relationship between rastering speed and elastic modulus (out of plane behavior) was investigated. Material processing variables were the same utilized in Example 7. FIG. 10 shows a graph showing the leaflet bending modulus for different values of mandrel tangential velocities (0.3, 1.5, 3 [m/s]) and rastering velocities (0, 0.25, 2.5 [cm/s]) n=3 mean±st.e. Comparison with porcine tricuspid valve values, (n=5 mean±st.e) shows the capacity of the mandrel design to recapitulate native valve bending modulus. While the elastic modulus was fairly insensitive to changes of mandrel velocity (FIG. 10), the rastering velocity dictated the bending rigidity showing the capacity of this new design to achieve physiologically relevant values of bending rigidity on stentless complex geometries. Data were produced with a custom made biological tissue bending device previously developed and validated in [Mirnajafi A et. al., The flexural rigidity of the aortic valve leaflet in the commissural region. Journal of Biomechanics Volume 39, Issue 16, 2006, Pages 2966-2973]. Test were conducted at room temperature, under quasi-static conditions, samples were continuously immersed in PBS during the test, curvature range was ±0.12, Eulero-Bernoulli theory was adopted for the moment-curvature characteristic. The biaxial testing and the bending rigidity characterization combined together showed the capacity to the method/prototype to de-couple and control in plane and out of plane engineered valve mechanics.

Example 9

Figure 11A:
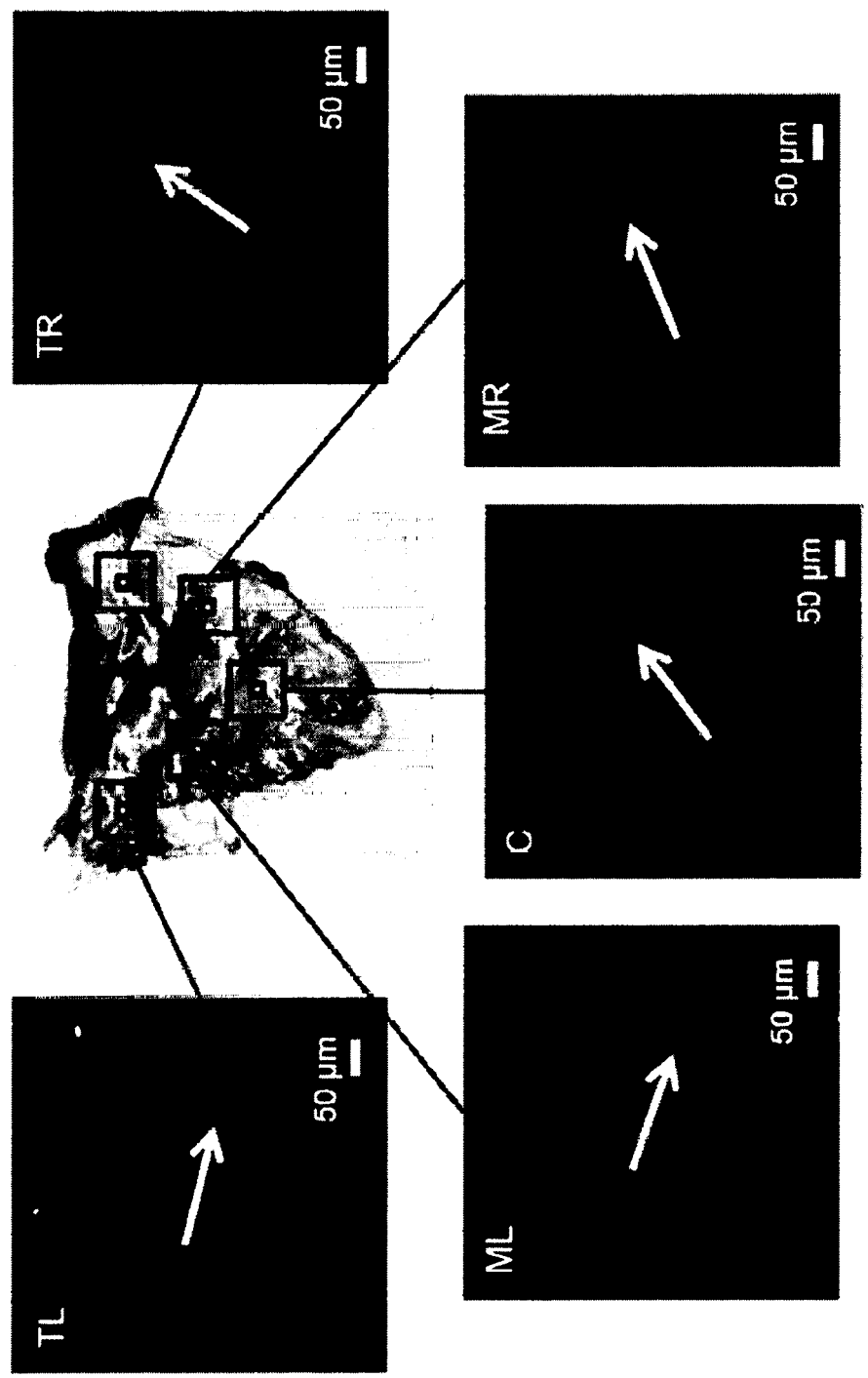
FIG. 11A provides multi-photon microscopy images of native porcine tricuspid valve micro-architecture showing collagen fibers network identified by acquiring collagen second harmonic generation. Volumes of 500 μm×500 μm×100 μm were analyzed on five different valves and on five different location within the valve leaflet including the commissures (top left TL and top right TR), the belly region (center C) and a transition zone between the two (mid-leaflet left ML and mid-leaflet right MR). The main direction of alignment (n=5 independent leaflets) is also indicated with a white arrow. Note the fibers rotation from the commissures to the belly region.
Figure 11B:
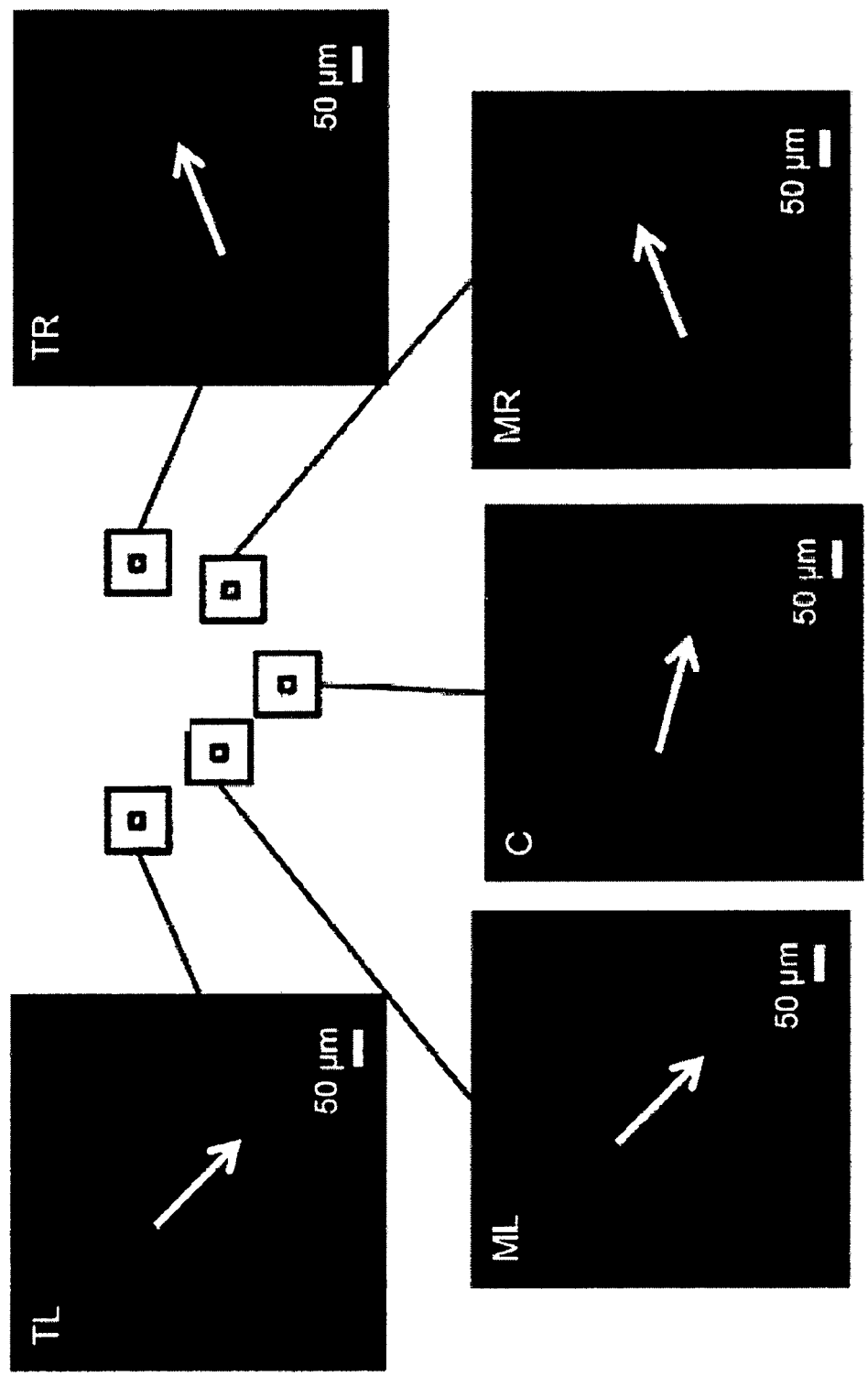
FIG. 11B provides multi-photon microscopy images of the engineered leaflets using the same imaging and digital analysis techniques as in FIG. 11A.

The engineered valve leaflets micro-architecture and a comparison with native porcine tricuspid valve are shown in FIGS. 11A and 11B. Material processing variables were the same utilized in Example 1. FIG. 11A are multi-photon microscopy images of native porcine tricuspid valve microarchitecture showing collagen fibers network identified by acquiring collagen second harmonic generation. Volumes of 500 μm×500 μm×100 μm were analyzed on five different valves and on five different location within the valve leaflet including the commissures (top left TL and top right TR), the belly region (center C) and a transition zone between the two (mid-leaflet left ML and mid-leaflet right MR). Collagen fibers shape was identified with the digital image analysis utilized in "Fiber micro-architecture in the longitudinal-radial and circumferential-radial planes of ascending thoracic aortic aneurysm media" by A Tsamis, et al. in Journal of biomechanics 46 (16), 2787-2794, the analysis method quantifies the main angle of fibers orientation with the mean of the fibers angle distribution θ as well as the level of fibers alignment with the Orientation Index (OI). This widely adopted metric (see for example "Characterization of the complete fiber network topology of planar fibrous tissues and scaffolds" by A D'Amore, et al in Biomaterials 31 (20), 5345-5354) is equal to 0.5 for a set of randomly oriented fibers and is equal to 1 for a set of parallel fibers. Values for the native tissue are reported in Table 2. The main directions of alignment (n=5 independent leaflets) are also indicated with white arrows. The fibers rotation are from the commissures to the belly region. FIG. 11B are multi-photon microscopy images of the engineered leaflets using the same imaging and digital analysis techniques as in FIG. 11A. FIGS. 11A and 11B use the same imaging and digital analysis technique. Not only the leaflets reported physiological levels of fiber alignment (Table 2: OI=0.57-0.62) but also the main angle of alignment showed a trend comparable to the native valve leaflets. This result cannot be achieved with conventional electrospinning electrodes (e.g. flat mats or rotating drums) where the main direction of alignment remains the same within the same construct.

TABLE 2

| | Native TV | | Engineered TV | |
|---|---|---|---|---|
| | ϑ (degrees) | OI | ϑ (degrees) | OI |
| TL | 76.0 ± 32.7 | 0.60 ± 0.04 | TL | 45.0 | 0.58 |
| ML | 70.7 ± 22.2 | 0.64 ± 0.15 | ML | 45.0 | 0.56 |
| C | 127.0 ± 13.0 | 0.60 ± 0.08 | C | 75.0 | 0.60 |
| MR | 111.7 ± 0.6 | 0.66 ± 0.04 | MR | 112.0 | 0.62 |
| TR | 144.3 ± 16.2 | 0.66 ± 0.08 | TR | 112.0 | 0.57 |

Example 10

Figure 12:
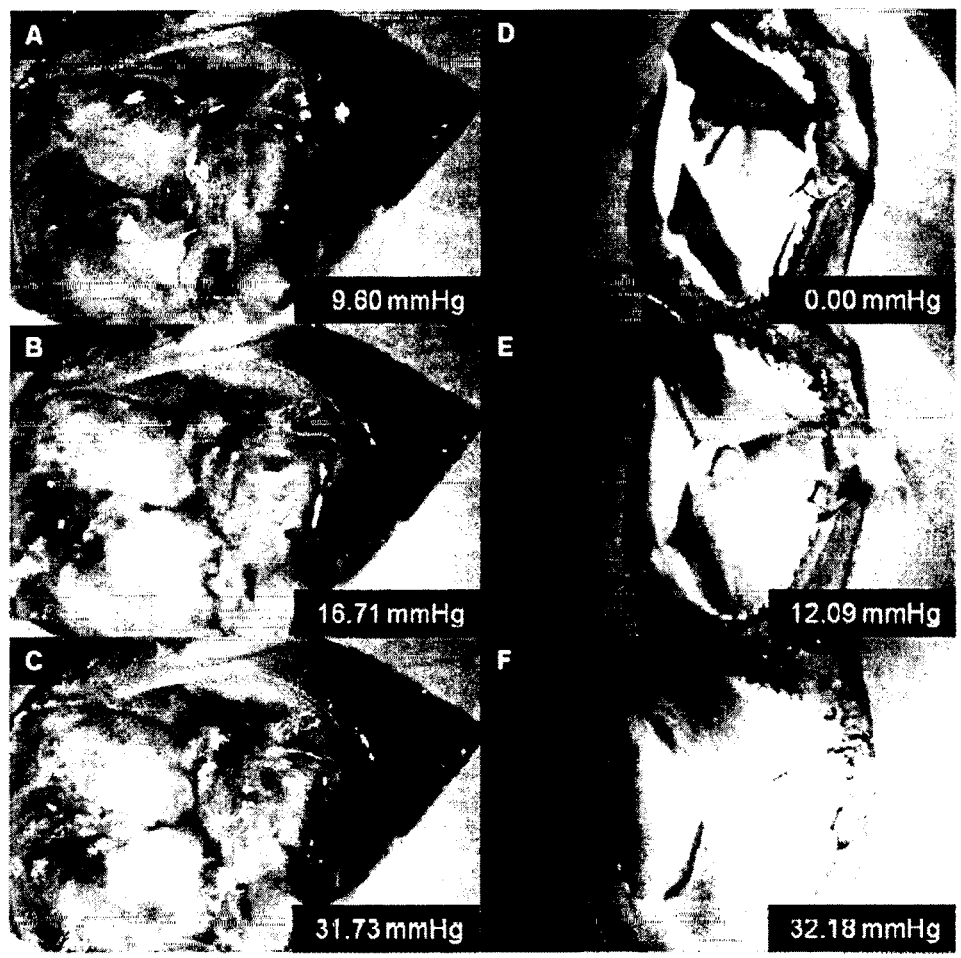
FIG. 12(A-F) provides photographic images showing engineered valve leaflets coaptation and suture retention ex-vivo testing. Electrospun valves were implanted ex vivo in tricuspid position on native porcine hearts, the right ventricle was gradually filled with saline, pressure values were monitored with a Millar pressure transducer (mikro-Cath™, Millar Inc. Houston Tex.) simultaneously, pictures of the coapting leaflets were acquired for healthy native porcine valves (A, B, C) and engineered valves (D, E, F) showing proper leaflets coaptation at Δp>30 mmHg and proper suture retention.

This Example shows the results of ex-vivo testing of engineered valve leaflet coaptation and suture retention (see, FIG. 12(A-F). Material processing variables were the same utilized in Example 1. Electrospun valves were implanted ex vivo in tricuspid position on native porcine hearts, the right ventricle was gradually filled with saline, pressure values were monitored with a Millar pressure transducer (mikroCath™, Millar Inc. Houston Tex.) simultaneously, pictures of the coapting leaflets were acquired for healthy native porcine valves (A, B, C) and engineered valves (D, E, F) showing proper leaflets coaptation at Δp>30 mmHg and proper suture retention.

Example 11

Figure 13:
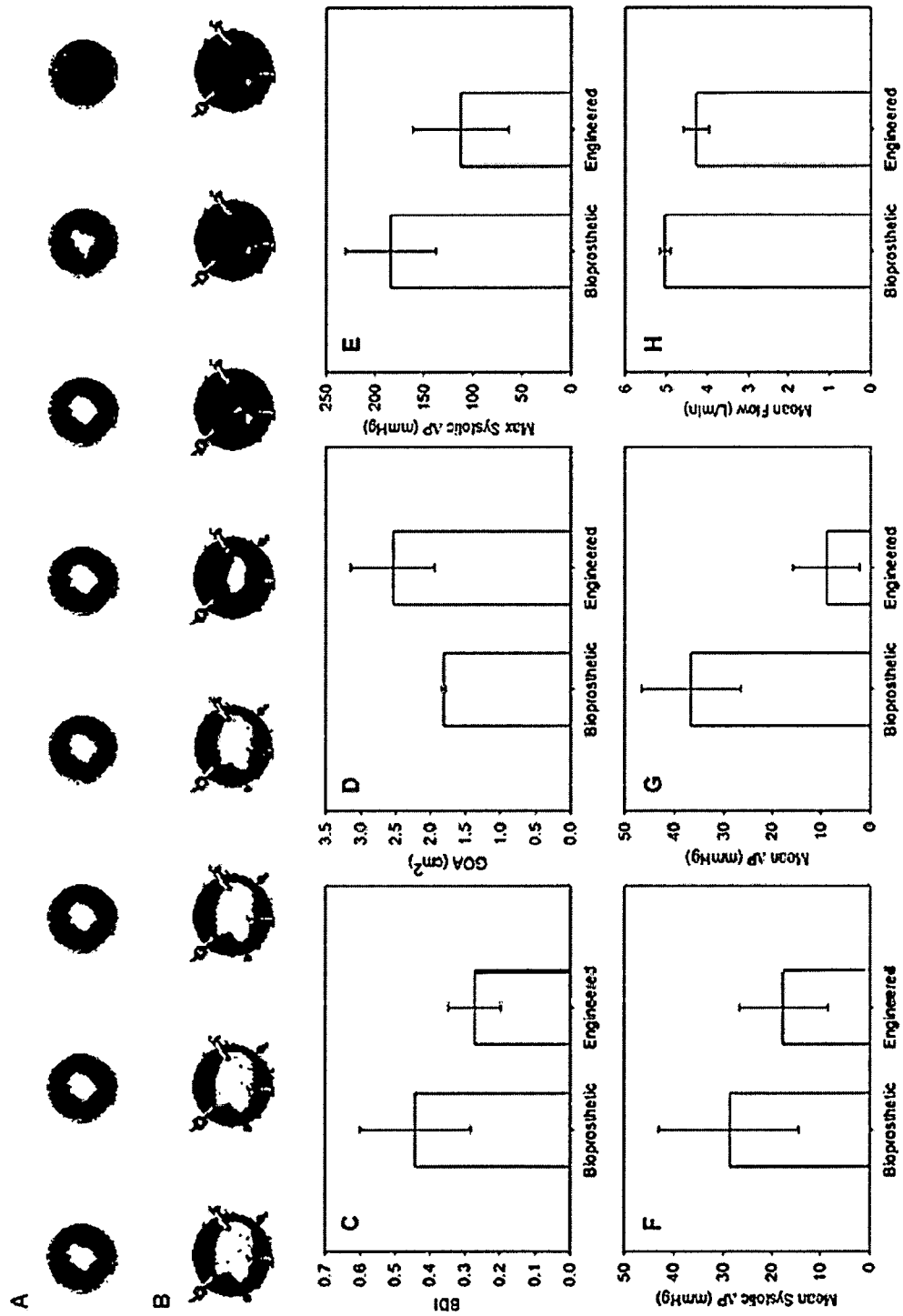
FIG. 13(A and B) provides graphical representations of valve function in vitro testing of (A) a state of the art commercial prosthetic valve dynamics (n=5, Carpentier-Edwards® Duraflex™) and (B) an engineered valve dynamics (n=3). Pulsatile flow across the valve was generated by the Thoratec Percutaneous VAD system, a commercial ventricular aided device operating at constant frequency of 70 beats/minutes. Two cameras detected continuously valve motion while pressure and flow were recorded by sensors. Digital image processing was performed with a dedicated Matlab code (Mathworks® Inc, Natick Mass.) to detect orifice area.

FIG. 13 provides graphical representations of valve function in vitro testing of (A) a state of the art commercial prosthetic valve dynamics (n=5, Carpentier-Edwards® Duraflex™) and (B) an engineered valve dynamics (n=3). Pulsatile flow across the valve was generated by the Thoratec Percutaneous VAD system, a commercial ventricular aided device operating at constant frequency of 70 beats/minutes. Two cameras detected continuously valve motion while pressure and flow were recorded by sensors. Digital image processing was performed with a dedicated Matlab code (Mathworks® Inc, Natick Mass.) to detect orifice area. FIGS. 14(A) and 14(B) show detected orifice areas (white) for the Carpentier-Edwards and Engineered Valve respectively during the systolic phase. FIG. 13(C) is a bar graph representation of the bending deformation index (BDI) for the Carpentier-Edwards bioprosthethic valve and the engineered valve of FIG. 13(A and B), respectively, BDI, which is a widely adopted metric for bending rigidity (see "In vitro hydrodynamics, cusp-bending deformation, and root distensibility for different types of aortic valve-sparing operations: Remodeling, sinus prosthesis, and reimplantation" by A. Erasmi et al. in The Journal of Thoracic and Cardiovascular Surgery Volume 130, Issue 4, October 2005, pp. 1044-1049), was calculated at the mid-diastole point. FIG. 13D is a bar graph representation of the geometric orifice area comparison (GEO) of the Carpentier-Edwards bioprosthethic valve and the engineered valve of FIG. 13(A and B), GEO were calculated from image processing illustrated in A-B at peak systole. FIG. 13(E) is a bar graph representation of the max systolic pressure of the Carpentier-Edwards bioprosthethic valve and the engineered valve of FIGS. 13A and 13B. FIG. 13F is a bar graph representation of the mean systolic pressure of the Carpentier-Edwards bioprosthethic valve and the engineered valve of FIG. 13(A and B). FIG. 13(G) is a bar graph representation of the mean pressure drop across the Carpentier-Edwards bioprosthethic valve and the engineered valve of FIG. 13(A and B) during a complete cycle including systole and diastole. FIG. 13(H) is a bar graph representation of the mean flow across the Carpentier-Edwards bioprosthethic valve and the engineered valve of FIG. 13(A and B) during a complete cycle including systole and diastole. None of the comparison presented in FIG. 13(C-H) showed statistically significant differences showing that the engineered valves have comparable dynamic function characteristics of a commercial bioprosthethic valve. This good dynamic performance was dictated by the capacity to control valve mechanics and anatomy discussed in this application.

Example 12

Figure 14:
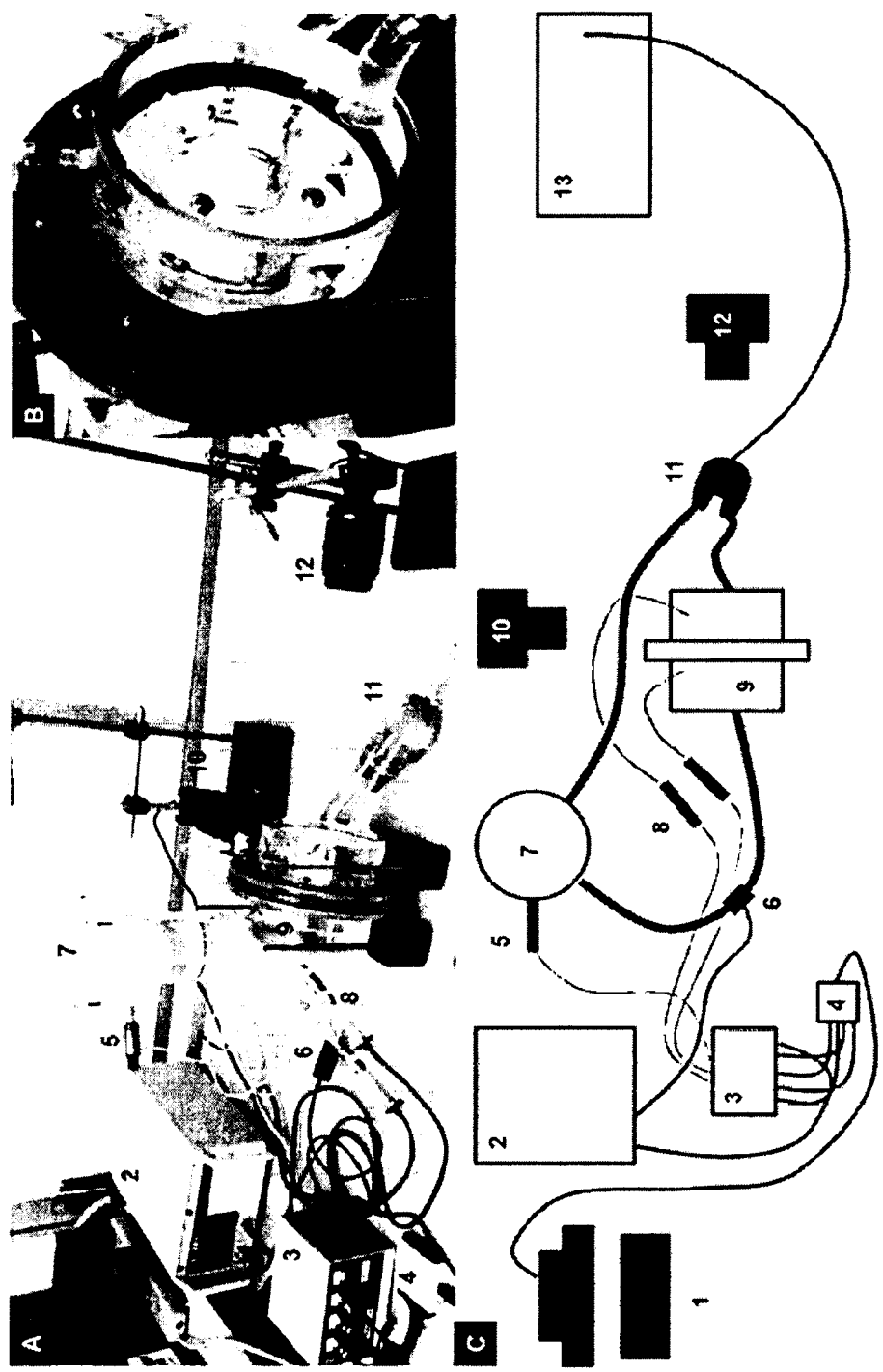
FIG. 14 shows (A) a photographic representation of a flow duplicator for valve functional assessment under physiological flow conditions, with a 40% glycerol solution being utilized to mimic blood viscosity, where 1) is a desktop computer, 2-4) represent pressure and flow signal acquisition system, 5) is pre-load pressure sensor, 6) is flow meter, 7) is a capacitor, 8) are pressure sensors, 9) is a valve holder with flanges, 10) is a side camera, 11) is Thoratec Percutaneous VAD System (Thoratec Corporation, Pleasanton, Calif.), 12) is a frontal camera, and 13) is VAD controller; (B) the engineered valve holding apparatus, wherein the white arrow points at the engineered valve; and (C) a schematic representation of the flow duplicator.

FIG. 14 shows (A) a photographic representation of a flow duplicator for valve functional assessment under physiological flow conditions, with a 40% glycerol solution being utilized to mimic blood viscosity, where 1) is a desktop computer, 2-4) represent pressure and flow signal acquisition system, 5) is pre-load pressure sensor, 6) is flow meter, 7) is a capacitor, 8) are pressure sensors, 9) is a valve holder with flanges, 10) is a side camera, 11) is Thoratec Percutaneous VAD System (Thoratec Corporation, Pleasanton, Calif.), 12) is a frontal camera, and 13) is VAD controller; (B) the engineered valve holding apparatus, wherein the white arrow points at the engineered valve; and (C) a schematic representation of the flow duplicator.

The present invention further includes the subject matter of the following clauses.

Clause 1: An electrodeposition target having a surface which comprises a pattern of conductive and non-conductive surface portions, wherein the target is attached to a mandrel having a rotational axis, and a spindle electrically connected to a conductive portion of the target.

Clause 2: The electrodeposition target of clause 1, in which the mandrel comprises a non-conductive sheath insulating at least a portion of the conductive portion.

Clause 3: The electrodeposition target of clause 2, in which the target comprises: a support portion disposed about the rotational axis of the mandrel; a conductive insert comprising a plurality ridges extending longitudinally from the support portion and a plurality of concave portions between the ridges; and a non-conductive layer over at least a portion of the support portion and at least a portion of the ridges.

Clause 4: The electrodeposition target of clause 3, in which the insert comprises two concave portions, wherein the two concave portions are symmetrical or asymmetrical about a rotation axis of the mandrel.

Clause 5: The electrodeposition target of clause 4, in which a cross-section of the target at the concave portions perpendicular to the rotational axis is "U"-shaped.

Clause 6: The electrodeposition target of any one of clauses 3-5, wherein the non-conductive layer is continuous around a perimeter of the plurality of concave portions.

Clause 7: The electrodeposition target of any one of clauses 3-6, in which the concave portions have the shape of a valvecusp, e.g., a normal or pathological valve cusp, such as a shape and size of a normal or pathological human or animal mitral, tricuspid, aortic, or pulmonary valve cusp (leaflet).

Clause 8: The electrodeposition target of any one of clauses 1-8 in which the target comprises:
a. a support portion having a non-conductive surface and a radius disposed about a rotational axis of the mandrel; and
b. a leaflet portion attached to and extending longitudinally from the support portion along the rotational axis, the leaflet portion comprising three concave, conductive portions defined by three conductive ridges extending radially from the rotational axis and having peaks, the leaflet portion comprising a first portion adjacent to and extending from the support portion and an optional second portion extending longitudinally from the first portion opposite the support portion, wherein the radius of the ridges of the first portion decreases no more than 10% from the support portion to the second portion, and the radius of the ridges in the second portion, when present decreases at least 50%, and optionally at least 60%, 70%, 75%, 80%, 90%, 95%, or 99% in the second portion, the ridges further comprising a non-conductive layer that extends from the support portion over at least a portion of the ridge peaks in the first portion.

Clause 9: The electrodeposition target of any one of clauses 1-8, in which the target comprises:
a. a support portion having a non-conductive surface and a radius disposed about a rotational axis of the mandrel; and
b. a leaflet portion attached to and extending longitudinally from the support portion along the rotational axis, the leaflet portion comprising two concave, conductive portions defined by two conductive ridges extending radially from the rotational axis and having peaks, the leaflet portion comprising a first portion adjacent to and extending from the support portion, wherein the radius of the ridges of the first portion decreases no more than 10% from the support portion to a distal end of the first portion, the ridges further comprising a non-conductive layer that extends from the support portion over at least a portion of the ridge peaks in the first portion.

Clause 10: The electrodeposition target of either of clauses 8 or 9, wherein the non-conductive layer is continuous around a perimeter of the concave, conductive portions.

Clause 11: The electrodeposition target of either of clauses 8 or 9, wherein the circumferential width of the ridges decreases in longitudinal distance from the cylindrical portion.

Clause 12: The electrodeposition target of either of clauses 8 or 9, in which the first portion has a radius substantially the same as the cylindrical portion.

Clause 13: The electrodeposition target of any of clauses 1-12, comprising an insulating sheath, and a removable conductive insert having a cylindrical portion and comprising the conductive ridges, the ridge peaks, and the concave conductive portions defined by the ridges, wherein the insulating sheath covers and insulates at least a portion of the non-conductive 1 portion of the insert and at least a portion of the ridge peaks of the ridges of the conductive insert.

Clause 14: The electrodeposition target of any of clauses 1-13, wherein the support portion is cylindrical.

Clause 15: The electrodeposition target of any of clauses 1-14, further comprising a flange extending radially about at least a portion of the support portion.

Clause 16: A prosthetic valve formed from a matrix of polymeric fibers, comprising:
a. a tubular (does not imply cylindrical, but can have a circular, oval or any closed shape in cross-section perpendicular to the longitudinal axis) support portion defining an aperture and having a longitudinal axis; and
b. at least two concave leaflets extending longitudinally from the support portion, wherein each leaflet comprises a concave central portion, a peripheral portion about the concave central portion, a proximal end connected to the support portion, and a distal end that is longitudinally distal to the support portion, wherein peripheral portions of adjacent leaflets are partially joined at and adjacent to the support portion forming commissures between adjacent leaflets.

Clause 17: The prosthetic valve of clause 16, wherein the leaflets have a bending modulus ranging from 500 kPA to 500000 kPa, a mechanical strain ranging from 0 to 100, and/or a stress ranging from 0 to 5000 kPa.

Clause 18: The valve of clause 16, wherein the matrix comprises an anisotropic portion with an orientation index ranging from 0.5 to 0.8.

Clause 19: The valve of any of clauses 16-18, wherein the matrix at the commissure and/or peripheral portions is anisotropic with fibers of the matrix being biased in a longitudinal direction, and/or the matrix in the concave central portion is anisotropic with fibers of the matrix being biased in a circumferential direction.

Clause 20: The valve of any of clauses 16-18 having two cusps, that are optionally assymetrical.

Clause 21: The valve of any of clauses 16-18 having three cusps, that are optionally assymetrical.

Clause 22: The valve of any of clauses 16-18, having two cusps shaped as mitral valve cusps, or having three cusps shaped as tricuspid valve cusps.

Clause 23: The valve of any of clauses 16-22, wherein the matrix is formed by electrospinning.

Clause 24: The prosthetic valve device of any of clauses 16-23, wherein the matrix comprises a polymer composition selected from a group consisting of one or more of poly(ester urethane) urea (PEUU), poly(ether ester urethane)urea (PEEUU), poly(ester carbonate)urethane urea (PECUU), poly(carbonate)urethane urea (PCUU), a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polyurethane, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin.

Clause 25: A method of making a valve structure comprising electrodepositing a matrix of a biodegradable, biocompatible polymer composition onto the electrodeposition target of any of clauses 1-9.

Clause 26: The method of clause 25, wherein the polymer composition comprises a synthetic polymer.

Clause 27: The method of clause 26, wherein the synthetic polymer selected from a group consisting of one or more of poly(ester urethane) urea (PEUU), poly(ether ester urethane) urea (PEEUU), poly(ester carbonate)urethane urea (PECUU), poly(carbonate)urethane urea (PCUU), a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(l-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polyurethane, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin Clause 28: The method of clause 26, wherein the synthetic polymer is a PEUU, PEEUU, PECUU or PCUU.

Clause 29: The method of any of clauses 25-28, where the polymer matrix is deposited with a directional bias at one or more locations on the target to produce one or more anisotropic portions.

Clause 30: The method of clause 29, wherein more than 50% of the direction of the electrodeposited polymer is circumferentially biased within a central portion of the concave portions and wherein more than 50% of the direction of the electrodeposited polymer is longitudinally biased at or near the commissures of the leaflet portions.

Clause 31: The method of any of clauses 25-30, wherein the shape and size of the concave portions of the electrodeposition target mimics native or pathological valve cusp shape and size of a human or animal valve.

Clause 32: The method of clause 31, in which the concave portions have a shape and size of a normal or pathological human or animal mitral, tricuspid, aortic, or pulmonary valve cusp (leaflet).

Clause 33: The method of any of clauses 25-32, further comprising removing the valve structure from the electrodeposition target and trimming the valve structure to separate distal ends of the leaflets Clause 34: The method of any of clauses 25-33, further comprising seeding the valve structure with cells, and optionally incubating the cells on the valve structure so that the cells coat and/or infiltrate at least a portion of the valve structure.

Clause 35: The method of any of clauses 25-34, further comprising electrodepositing, spraying or otherwise adding or incorporating a second polymer composition, an ECM gel, a drug, water, saline, PBS, cell culture medium, cells, biologics, salts, buffers, cytokines, growth factors, or combinations thereof onto the electrodeposition target.

Clause 36: A method of repairing or replacing a heart valve in a patient, comprising implanting a heart valve prosthesis according to clause 16-24 in a patient.

Clause 37: The method of clause 36, in this the valve prosthesis is a heart valve prosthesis.

Clause 38: The method of clauses 36 or 37, in which the implanting is performed by a percutaneous route.

Clause 39: The method of any of clauses 36-38, in which the implanting is a stentless replacement of a native heart valve.

Clause 40: The method of clause 39, in which the heart valve prosthesis is sewn to one or more of a patient's heart valve annulus, and optionally one or more of papillary muscles for atrio-ventricular valves or the commissures for ventriculo-arterial valves.

Clause 41: The method of clauses 36 or 37, in which the valve is mounted prior to implantation in a structured frame, and the structured frame containing the valve is attached, e.g. sewn, to a patient's valve annulus.

Clause 42: Use of the valve prosthesis of any of clauses 16-24 in any of the methods of clauses 36-41.

We claim:

1. An electrodeposition target having a surface which comprises a pattern of conductive and non-conductive surface portions,
   wherein the target comprises:
      a conductive body comprising a plurality of longitudinally extending ridges and concave portions between the plurality of ridges, and
      a non-conductive covering over at least portions of the plurality of ridges,
   wherein surfaces of the concave portions of the conductive body are uncovered, and
   wherein the target is attached to a mandrel having a rotational axis, and a spindle electrically connected to a conductive portion of the target.

2. The electrodeposition target of claim 1, wherein the target further comprises a support portion disposed about the rotational axis of the mandrel,
   wherein the conductive body comprises a conductive insert comprising (i) the plurality of ridges, which extend longitudinally from the support portion, and (ii) the concave portions between the ridges; and
   wherein the non-conductive covering comprises a non-conductive layer over at least a portion of the support portion and at least a portion of the plurality of ridges.

3. The electrodeposition target of claim 2, in which the insert comprises two concave portions, wherein the two concave portions are symmetrical or asymmetrical about a rotation axis of the mandrel.

4. The electrodeposition target of claim 2, in which the concave portions have a shape of at least one of a normal or pathological human or animal mitral, tricuspid, aortic, or pulmonary valve cusp.

5. The electrodeposition target of claim 1, wherein the target further comprises at least one support portion having a non-conductive surface and a radius disposed about a rotational axis of the mandrel,
   wherein the conductive body comprises at least one leaflet portion attached to and extending longitudinally from the support portion along the rotational axis, the at least one leaflet portion comprising:
      three concave, conductive portions defined by three conductive ridges extending radially from the rotational axis and having ridge peaks,
      a first portion adjacent to and extending from the support portion, and
      a second portion extending longitudinally from the first portion opposite the support portion, and
   wherein the radius of the ridges of the first portion decreases no more than 10% from the support portion to the second portion, and the radius of the ridges in the second portion decreases at least 50%.

6. The electrodeposition target of claim 5, wherein the non-conductive covering comprises an insulating sheath,
   wherein the conductive body comprises a removable insert, the removable insert comprising a cylindrical portion, the conductive ridges of the at least one leaflet portion, the ridge peaks of the leaflet portion, and the concave conductive portions defined by the ridges, and wherein the insulating sheath covers and insulates at least a portion of a non-conductive portion of the removable insert and at least a portion of the ridge peaks of the ridges.

7. The electrodeposition target of claim 5, wherein the non-conductive covering comprises a non-conductive layer that extends from the support portion over at least a portion of the ridge peaks in the first portion.

8. The electrodeposition target of claim 1, wherein the target further comprises at least one support portion having a non-conductive surface;

wherein the conductive body comprises at least one leaflet portion attached to and extending longitudinally from the support portion along the rotational axis, wherein the leaflet portion comprises:
two concave, conductive portions defined by two conductive ridges extending radially from the rotational axis and having peaks, and
a first portion adjacent to and extending from the support portion, and wherein the non-conductive covering comprises a non-conductive layer that extends from the support portion over at least a portion of the ridge peaks in the first portion.

9. The electrodeposition target of claim 1, wherein the conductive and non-conductive surface portions of the target surface are configured such that a valve construct produced by electrodeposition of polymer fibers onto the target comprises at least one portion where the polymer fibers are aligned in a circumferential direction and at least one portion in which the polymer fibers are non-directional or in an isotropic pattern.

10. The electrodeposition target of claim 1, wherein the conductive and non-conductive surface portions of the target surface are configured such that a valve construct produced by electrodeposition of polymer fibers onto the target comprises at least a first region in which the polymer fibers are circumferentially aligned and at least a second region in which the polymer fibers are oriented longitudinally.

11. The electrodeposition target of claim 9, wherein the first region of the valve construct comprises a leaflet belly region and the second region of the valve construct comprises a commissure region.

12. The electrodeposition target of claim 1, wherein the conductive surface portion comprises metal, and the non-conductive covering comprises an insulating polymer material.

* * * * *

UNITED STATES PATENT AND TRADEMARK OFFICE
CERTIFICATE OF CORRECTION

PATENT NO. : 11,129,711 B2
APPLICATION NO. : 15/553799
DATED : September 28, 2021
INVENTOR(S) : Vinay Badhwar et al.

It is certified that error appears in the above-identified patent and that said Letters Patent is hereby corrected as shown below:

On the Title Page

Column 1, Assignees, Line 3, after "Education" insert -- , Pittsburgh, PA (US) --

Column 1, Assignees, Line 3, after "Foundation" insert -- , (IT) --

In the Specification

Column 1, Line 9, delete "file" and insert -- filed --

In the Claims

Column 36, Line 32, Claim 2, delete "ridges;" and insert -- ridges, --

Column 37, Line 13, Claim 8, delete "surface;" and insert -- surface, --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*